(12) United States Patent
Geva et al.

(10) Patent No.: US 10,303,971 B2
(45) Date of Patent: May 28, 2019

(54) IMAGE CLASSIFICATION BY BRAIN COMPUTER INTERFACE

(71) Applicant: InnerEye Ltd., Herzeliya Pituach (IL)

(72) Inventors: Amir B. Geva, Tel-Aviv (IL); Leon Y. Deouell, Tel-Aviv (IL); Sergey Vaisman, Ramat-Gan (IL); Omri Harish, Zur Yigal (IL); Ran El Manor, Savyon (IL); Eitan Netzer, Kiryat-Tivon (IL); Shani Shalgi, Hod-HaSharon (IL)

(73) Assignee: InnerEye Ltd., Herzeliya Pituach (IL)

( * ) Notice: Subject to any disclaimer, the term of this patent is extended or adjusted under 35 U.S.C. 154(b) by 0 days.

(21) Appl. No.: 15/579,226

(22) PCT Filed: Jun. 2, 2016

(86) PCT No.: PCT/IL2016/050569
§ 371 (c)(1),
(2) Date: Dec. 4, 2017

(87) PCT Pub. No.: WO2016/193979
PCT Pub. Date: Dec. 8, 2016

(65) Prior Publication Data
US 2018/0089531 A1    Mar. 29, 2018

(30) Foreign Application Priority Data
Jun. 3, 2015 (IL) .......................... 239191

(51) Int. Cl.
*A61B 5/00* (2006.01)
*G06F 3/01* (2006.01)
(Continued)

(52) U.S. Cl.
CPC ........ *G06K 9/4628* (2013.01); *A61B 5/04017* (2013.01); *A61B 5/04842* (2013.01);
(Continued)

(58) Field of Classification Search
CPC .... G09K 9/2054; G09K 9/4628; G09K 9/627; G06N 3/04; G06N 3/08; G06F 3/015
See application file for complete search history.

(56) References Cited

U.S. PATENT DOCUMENTS 7,835,581 B2    11/2010 Mathan et al.
7,991,195 B2    8/2011 Mathan et al.
(Continued)

FOREIGN PATENT DOCUMENTS

CN        103019383 A  *  4/2013
WO    WO 2014/142962      9/2014
WO    WO 2016/193979     12/2016

OTHER PUBLICATIONS

Cheemalapati et al. ("A real-time classification algorithm for emotion detection using portable EEG," IEEE 14th International Conference on Information Reuse and Integration, Aug. 14-16, 2013).*
(Continued)

*Primary Examiner* — Yubin Hung

(57) ABSTRACT

A method of classifying an image is disclosed. The method comprises: applying a computer vision procedure to the image to detect therein candidate image regions suspected as being occupied by a target; presenting to an observer each candidate image region as a visual stimulus, while collecting neurophysiological signals from a brain of the observer; processing the neurophysiological signals to identify a neurophysiological event indicative of a detection of the target by the observer; and determining an existence of the target in the image is based, at least in part, on the identification of the neurophysiological event.

21 Claims, 21 Drawing Sheets
(16 of 21 Drawing Sheet(s) Filed in Color)

(51) Int. Cl.
  *G06K 9/46* (2006.01)
  *A61B 5/04* (2006.01)
  *A61B 5/0484* (2006.01)
  *A61B 5/11* (2006.01)
  *G06K 9/20* (2006.01)
  *G06K 9/62* (2006.01)
  *G06N 3/04* (2006.01)
  *G06N 3/08* (2006.01)
  *G06K 9/00* (2006.01)
  *G16H 30/40* (2018.01)
  *G06N 7/00* (2006.01)

(52) U.S. Cl.
  CPC ............ *A61B 5/1103* (2013.01); *A61B 5/486* (2013.01); *A61B 5/7264* (2013.01); *G06F 3/01* (2013.01); *G06K 9/00671* (2013.01); *G06K 9/2054* (2013.01); *G06K 9/627* (2013.01); *G06K 9/6247* (2013.01); *G06K 9/6272* (2013.01); *G06N 3/0454* (2013.01); *G06N 3/088* (2013.01); *G06F 3/015* (2013.01); *G06N 3/04* (2013.01); *G06N 3/08* (2013.01); *G06N 7/005* (2013.01); *G16H 30/40* (2018.01)

(56) References Cited

U.S. PATENT DOCUMENTS

| | | | |
|---|---|---|---|
| 8,059,136 B2 | 11/2011 | Mathan | |
| 8,214,309 B1 | 7/2012 | Khosla et al. | |
| 8,244,475 B2 | 8/2012 | Aguilar et al. | |
| 8,254,634 B2 | 8/2012 | Mathan et al. | |
| 8,271,074 B2 | 9/2012 | Mathan et al. | |
| 8,335,751 B1 | 12/2012 | Daily et al. | |
| 8,374,687 B2 | 2/2013 | Mathan et al. | |
| 8,467,607 B1* | 6/2013 | Toshev et al. ........ G06K 9/4642 382/173 |
| 8,671,069 B2 | 3/2014 | Chang et al. | |
| 8,699,767 B1 | 4/2014 | Khosla et al. | |
| 8,731,650 B2 | 5/2014 | Sajda et al. | |
| 2006/0111644 A1* | 5/2006 | Guttag ................... A61B 5/048 600/544 |
| 2006/0281980 A1* | 12/2006 | Randlov ............ A61B 5/14532 600/301 |
| 2007/0086624 A1* | 4/2007 | Breed ................. G06K 9/00362 382/104 |
| 2007/0173699 A1 | 7/2007 | Mathan et al. | |
| 2009/0003699 A1* | 1/2009 | Dugan ................... G01N 23/06 382/173 |
| 2009/0150821 A1 | 6/2009 | Mathan | |
| 2009/0232348 A1* | 9/2009 | Abraham ................. G06K 9/00 382/100 |
| 2010/0100001 A1* | 4/2010 | Aguilar .................. A61B 3/113 600/544 |
| 2010/0278425 A1* | 11/2010 | Takemoto ................ G06T 7/10 382/173 |
| 2011/0118636 A1* | 5/2011 | Kitamura ......................... 601/84 |
| 2011/0206240 A1* | 8/2011 | Hong ................. G06K 9/00771 382/103 |
| 2011/0238685 A1 | 9/2011 | Garcia Molina et al. | |
| 2012/0022343 A1 | 1/2012 | Shastri et al. | |
| 2012/0089552 A1* | 4/2012 | Chang ............... G06F 17/30817 706/52 |
| 2012/0108997 A1* | 5/2012 | Guan ................. A61B 5/04014 600/545 |
| 2012/0172743 A1* | 7/2012 | Aguilar .................. A61B 5/048 600/544 |
| 2013/0158883 A1* | 6/2013 | Hasegawa ............ A61B 5/0476 702/19 |
| 2013/0247173 A1* | 9/2013 | Jakobsson ............... G06F 21/45 726/18 |
| 2013/0300939 A1* | 11/2013 | Chou ................. G06K 9/00765 348/700 |
| 2013/0346168 A1* | 12/2013 | Zhou ....................... G06F 1/163 705/14.4 |
| 2015/0088024 A1* | 3/2015 | Sackellares .......... A61B 5/0476 600/544 |
| 2015/0199010 A1* | 7/2015 | Coleman .............. A61B 5/0006 345/156 |
| 2015/0277560 A1* | 10/2015 | Beaty ...................... G06F 3/015 345/156 |
| 2016/0051163 A1* | 2/2016 | Deouell ............... A61B 5/7203 600/544 |
| 2016/0077547 A1* | 3/2016 | Aimone .................. G06F 3/012 345/8 |
| 2016/0103487 A1* | 4/2016 | Crawford ................ G06F 3/015 600/544 |
| 2017/0091528 A1* | 3/2017 | Savvides ............ G06K 9/00147 |
| 2017/0188933 A1* | 7/2017 | Huggins .............. A61B 5/4088 |

OTHER PUBLICATIONS

Alpert et al. ("Spatiotemporal Representations of Rapid Visual Target Detection a Single-Trial EEG Classification Algorithm," IEEE Transactions on Biomedical Engineering, vol. 61, Issue 8, Nov. 7, 2013, pp. 2290-2303).*
Cecotti et al. ("Convolutional Neural Networks for P300 Detection with Application to Brain-Computer Interfaces," IEEE Transactions on Pattern Analysis and Machine Intelligence, vol. 33, Issue 3, Mar. 2011(Date of Publication: Jun. 28, 2010)).*
Bigdely-Shamlo et al. ("Brain Activity-Based Image Classification From Rapid Serial Visual Presentation," IEEE Transactions on Neural Systems and Rehabilitation Engineering, vol. 16, Issue 5, Aug. 12, 2008, pp. 432-441).*
Bevilacqua et al. ("A novel BCI-SSVEP based approach for control of walking in Virtual Environment using a Convolutional Neural Network," 2014 International Joint Conference on Neural Networks (IJCNN), Jul. 6-11, 2014).*
Ren et al. ("Convolutional deep belief networks for feature extraction of EEG signal," 2014 International Joint Conference on Neural Networks (IJCNN), Jul. 6-11, 2014).*
Cecotti et al. ("Single-Trial Classification of Event-Related Potentials in Rapid Serial Visual Presentation Tasks Using Supervised Spatial Filtering," IEEE Transactions on Neural Networks and Learning Systems, vol. 25, Issue 11, Nov. 2014 (Date of Publication: Feb. 19, 2014)).*
Zhang et al. ("EMG parameters and EEG α Index change at fatigue period during different types of muscle contraction," SPIE Proceedings vol. 7999, Saratov Fall Meeting 2010: Optical Technologies in Biophysics and Medicine XII, Apr. 12, 2011).*
Hope et al. ("High throughput screening for mammography using a human-computer interface with rapid serial visual presentation (RSVP)," Proc. SPIE. 8673, Medical Imaging 2013: Image Perception, Observer Performance, and Technology, Mar. 28, 2013).*
Liu et al. ("Deep learning EEG response representation for brain computer interface," Proceedings of the 34th Chinese Control Conference, Jul. 28-30, 2015).*
International Preliminary Report on Patentability dated Dec. 14, 2017 From the International Bureau of WIPO Re. Application No. PCT/IL2016/050569. (6 Pages).
International Search Report and the Written Opinion dated Sep. 28, 2016 From the International Searching Authority Re. Application No. PCT/IL2016/050569.
Csurka et al. "Visual Categorization with Bags of Keypoints", Workshop on Statistica Learning in Computer Vision, ECCV, Prague, Czechia, Oct. 1, 2004, : Oct. 1-22, 2004.
Communication Pursuant to Rule 164(1) EPC: Supplementary Partial European Search Report and the European Provisional Opinion dated Jan. 17, 2019 From the European Patent Office Re. Application No. 16802693.8. (15 Pages).
Chan et al. "An Overview of Brain Computer Interfaces", Proceedings of 30th International Conference on Computers and Their Applications, XP055537805, pp. 1-7, Mar. 9, 2015.
Kapoor et al. "Combining Brain Computer Interfaces with Vision for Object Categorization", Computer Vision and Pattern Recognition, 2008. CVPR 2008. IEEE Conference on. IEEE, XP031297176, pp. 1-8, Jun. 23, 2008.

(56) References Cited

OTHER PUBLICATIONS

Wang et al. "A Closed-loop System for Rapid Face Retrieval by Combining EEG and Computer Vision", 2015 7th International IEEE/EMBS Conference on Neural Engineering (NER), IEEE, XP033166181, pp. 130-133, Apr. 22, 2015.

* cited by examiner

IMAGE CLASSIFICATION BY BRAIN COMPUTER INTERFACE

RELATED APPLICATIONS

This application is a National Phase of PCT Patent Application No. PCT/IL2016/050569 having International filing date of Jun. 2, 2016, which claims the benefit of priority of Israeli Patent Application No. 239191 filed Jun. 3, 2015. The contents of the above applications are all incorporated by reference as if fully set forth herein in their entirety.

FIELD AND BACKGROUND OF THE INVENTION

The present invention, in some embodiments thereof, relates to a Brain Computer Interface (BCI) and, more particularly, but not exclusively, to a method and system for classification of an image.

BCI applications depend on decoding brain activity in response to single events (trials), as opposed to delineation of the average response frequently studied in basic research. Electroencephalography (EEG), a noninvasive recording technique, is one of the commonly used systems for monitoring brain activity. EEG data is simultaneously collected from a multitude of channels at a high temporal resolution, yielding high dimensional data matrices for the representation of single trial brain activity. In addition to its unsurpassed temporal resolution, EEG is non-invasive, wearable, and more affordable than other neuroimaging techniques, and is thus a prime choice for any type of practical BCI.

Traditional classification techniques use machine-learning algorithms to classify single-trial spatio-temporal activity matrices based on statistical properties of those matrices. These methods are based on two main components: a feature extraction mechanism for effective dimensionality reduction, and a classification algorithm. Typical classifiers use a sample data to learn a mapping rule by which other test data can be classified into one of two or more categories. Classifiers can be roughly divided to linear and non-linear methods. Non-linear classifiers, such as Neural Networks, Hidden Markov Model and k-nearest neighbor, can approximate a wide range of functions, allowing discrimination of complex data structures. While non-linear classifiers have the potential to capture complex discriminative functions, their complexity can also cause overfitting and carry heavy computational demands, making them less suitable for real-time applications.

Linear classifiers, on the other hand, are less complex and are thus more robust to data overfitting. Linear classifiers perform particularly well on data that can be linearly separated. Fisher Linear discriminant (FLD), linear Support Vector Machine (SVM) and Logistic Regression (LR) are examples of linear classifiers. FLD finds a linear combination of features that maps the data of two classes onto a separable projection axis. The criterion for separation is defined as the ratio of the distance between the classes mean to the variance within the classes. SVM finds a separating hyper-plane that maximizes the margin between the two classes. LR, as its name suggests, projects the data onto a logistic function.

International publication No. WO2014/170897, the contents of which are hereby incorporated by reference, discloses a method for conduction of single trial classification of EEG signals of a human subject generated responsive to a series of images containing target images and non-target images. The method comprises: obtaining the EEG signals in a spatio-temporal representation comprising time points and respective spatial distribution of the EEG signals; classifying the time points independently, using a linear discriminant classifier, to compute spatio-temporal discriminating weights; using the spatio-temporal discriminating weights to amplify the spatio-temporal representation by the spatio-temporal discriminating weights at tempo-spatial points respectively, to create a spatially-weighted representation; using Principal Component Analysis (PCA) on a temporal domain for dimensionality reduction, separately for each spatial channel of the EEG signals, to create a PCA projection; applying the PCA projection to the spatially-weighted representation onto a first plurality of principal components, to create a temporally approximated spatially weighted representation containing for each spatial channel, PCA coefficients for the plurality of principal temporal projections; and classifying the temporally approximated spatially weighted representation, over the number of channels, using the linear discriminant classifier, to yield a binary decisions series indicative of each image of the images series as either belonging to the target image or to the non-target image.

SUMMARY OF THE INVENTION

According to an aspect of some embodiments of the present invention there is provided a method of classifying an image. The method comprises: applying a computer vision procedure to the image to detect therein candidate image regions suspected as being occupied by a target; presenting to an observer each candidate image region as a visual stimulus, while collecting neurophysiological signals from a brain of the observer; processing the neurophysiological signals to identify a neurophysiological event indicative of a detection of the target by the observer; and determining an existence of the target in the image is based, at least in part, on the identification of the neurophysiological event.

According to some embodiments of the invention the invention the method comprises tiling the image into a plurality of image tiles, wherein at least one tile encompasses a candidate image region, and wherein the presenting each candidate image region comprises presenting the at least one tile.

According to some embodiments of the invention the invention the method comprises assigning to the image a neurophysiological detection score, wherein the determining the existence of the target in the image is based, at least in part on the neurophysiological detection score.

According to some embodiments of the invention the invention the method comprises assigning a computer detection score to the image using the computer vision procedure, wherein the determining the existence of the target in the image is based on both the computer detection score and the neurophysiological detection score.

According to some embodiments of the invention the invention the method comprises, for at least one image region or group of image regions, comparing the computer detection score to the neurophysiological detection score, and re-presenting the at least one image region or group of image regions to the observer based on the comparison.

According to some embodiments of the invention the invention the method comprises processing the neurophysiological signals to identify eye blinks, and re-presenting an image region or a group of image regions to the observer in response to a positive identification of the eye blink during previous presentation of the image region or group of image regions.

According to some embodiments of the invention the invention the method comprises repeating the presentation and the identification of the neurophysiological event for at least one image region of the set, comparing the identification to a previous identification of the at least one image region, and determining a neurophysiological state of the observer based on the comparison.

According to some embodiments of the invention the invention the method comprises presenting to the observer a database image region containing the target, processing the neurophysiological signals to identify a neurophysiological event indicative of a detection of the target in the database image region by the observer, and determining a neurophysiological state of the observer based on the identification.

According to some embodiments of the invention the invention the method comprises processing the neurophysiological signals to identify muscle tonus, and re-presenting an image region or a group of image regions to the observer in response to a positive identification of the muscle tonus during previous presentation of the image region or group of image regions.

According to an aspect of some embodiments of the present invention there is provided a method of classifying an image. The method comprises: applying a computer vision procedure to the image to detect a target therein, and assigning a computer detection score to the image using the computer vision procedure; presenting the image to an observer as a visual stimulus, while collecting neurophysiological signals from a brain of the observer; processing the neurophysiological signals to identify a neurophysiological event indicative of a detection of the target by the observer, and assigning to the image a neurophysiological detection score, based on the identification; and determining an existence of the target in the image based on both the computer detection score and the neurophysiological detection score.

According to some embodiments of the invention the invention the method comprises comparing the computer detection score to the neurophysiological detection score, and re-presenting the image to the observer based on the comparison.

According to some embodiments of the invention the invention the method comprises processing the neurophysiological signals to identify eye blinks, and re-presenting the image to the observer in response to a positive identification of the eye blink during previous presentation of the image.

According to some embodiments of the invention the invention the method comprises repeating the presentation and the identification of the neurophysiological event, comparing the identification to a previous identification of the image, and determining a neurophysiological state of the observer based on the comparison.

According to some embodiments of the invention the invention the neurophysiological signals comprise EEG signals, and wherein the method comprises calculating a ratio of slow wave EEG to fast wave EEG and determining a neurophysiological state of the observer based on the ratio.

According to some embodiments of the invention the invention the method comprises presenting to the observer a database image containing the target, processing the neurophysiological signals to identify a neurophysiological event indicative of a detection of the target in the database image by the observer, and determining a neurophysiological state of the observer based on the identification.

According to some embodiments of the invention the invention the method comprises processing the neurophysiological signals to identify muscle tonus, and re-presenting the image to the observer in response to a positive identification of the muscle tonus during previous presentation of the image.

According to some embodiments of the invention the invention the neurophysiological signals comprise EEG signals, and wherein the method comprises calculating a ratio of slow wave EEG to fast wave EEG and determining a neurophysiological state of the observer based on the ratio.

According to some embodiments of the invention the invention the method comprises processing the neurophysiological signals to identify eye blinks, evaluating a temporal pattern of the eye blinks and determining a neurophysiological state of the observer based on the temporal pattern.

According to some embodiments of the invention the invention the computer vision procedure employs clustering.

According to some embodiments of the invention the invention, wherein the computer vision procedure employs neural networks.

According to some embodiments of the invention the invention, wherein the collecting the neurophysiological signals is at a sampling rate of at least 150 Hz.

According to some embodiments of the invention the invention the method comprises applying a low pass filter to the collected neurophysiological signals.

According to some embodiments of the invention the invention the processing the neurophysiological signals comprises applying a Spatially Weighted Fisher Linear Discriminant (SWFLD) classifier to the neurophysiological signals.

According to some embodiments of the invention the invention the processing the neurophysiological signals comprises applying a convolutional neural network (CNN) classifier to the neurophysiological signals.

According to some embodiments of the invention the invention the processing the neurophysiological signals comprises: applying a Spatially Weighted Fisher Linear Discriminant (SWFLD) classifier; calculating a SWFLD classification score based on the SWFLD classifier; applying a convolutional neural network (CNN) classifier to the neurophysiological signals; calculating a CNN classification score based on the CNN classifier; and combining the SWFLD score and the CNN score.

According to some embodiments of the invention the invention the CNN comprises a first convolution layer applying spatial filtering for each of a plurality of time points characterizing the neurophysiological signals, a second convolution layer applying temporal filtering to outputs provided by the first convolution layer, and a third convolution layer applying temporal filtering to outputs provided by the second convolution layer.

According to some embodiments of the invention the invention the method comprises presenting to the observer a feedback regarding the identification of the neurophysiological event.

According to an aspect of some embodiments of the present invention there is provided a system for classifying an image. The system comprises: a data processor configured for applying a computer vision procedure to the image to detect therein image regions suspected as being occupied by a target, thereby providing a set of candidate image regions; a display communicating with the data processor, wherein the data processor is configured for presenting to an observer, by the display, each candidate image region as a visual stimulus; and a neurophysiological signal collection system, communicating with the data processor and being configured for collecting neurophysiological signals from a brain of the observer during the presentation and transmitting the signals to the data processor; wherein the data processor is configured for processing the neurophysiological signals to identify a neurophysiological event indicative of a detection of the target by the observer, and for determining an existence of the target in the image is based, at least in part, on the identification of the neurophysiological event.

According to some embodiments of the invention the data processor is configured for tiling the image into a plurality of image tiles, wherein at least one tile encompasses a candidate image region, and wherein the presenting each candidate image region comprises presenting the at least one tile.

According to some embodiments of the invention the invention the data processor is configured for assigning to the image a neurophysiological detection score, wherein the determining the existence of the target in the image is based, at least in part on the neurophysiological detection score.

According to some embodiments of the invention the data processor is configured for assigning a computer detection score to the image using the computer vision procedure, wherein the determining the existence of the target in the image is based on both the computer detection score and the neurophysiological detection score.

According to some embodiments of the invention the data processor is configured for comparing the computer detection score to the neurophysiological detection score, and re-presenting at least one image region or group of image regions to the observer based on the comparison.

According to some embodiments of the invention the invention the data processor is configured for processing the neurophysiological signals to identify eye blinks, and re-presenting an image region or a group of image regions to the observer in response to a positive identification of the eye blink during previous presentation of the image region or group of image regions.

According to some embodiments of the invention the invention the data processor is configured for repeating the presentation and the identification of the neurophysiological event for at least one image region of the set, for comparing the identification to a previous identification of the at least one image region, and for determining a neurophysiological state of the observer based on the comparison.

According to some embodiments of the invention the invention the data processor is configured for presenting to the observer a database image region containing the target, for processing the neurophysiological signals to identify a neurophysiological event indicative of a detection of the target in the database image region by the observer, and for determining a neurophysiological state of the observer based on the identification.

According to some embodiments of the invention the invention the data processor is configured for processing the neurophysiological signals to identify muscle tonus, and for re-presenting an image region or a group of image regions to the observer in response to a positive identification of the muscle tonus during previous presentation of the image region or group of image regions.

According to an aspect of some embodiments of the present invention there is provided a system of classifying an image, comprises: a data processor configured for applying a computer vision procedure to the image to detect a target therein, and assigning a computer detection score to the image using the computer vision procedure; a display system, communicating with the data processor, wherein the data processor is configured for presenting the image to an observer as a visual stimulus; a neurophysiological signal collection system, communicating with the data processor and being configured for collecting neurophysiological signals from a brain of the observer during the presentation and transmitting the signals to the data processor; wherein the data processor is configured for processing the neurophysiological signals to identify a neurophysiological event indicative of a detection of the target by the observer, assigning to the image a neurophysiological detection score, based on the identification, and determining an existence of the target in the image based on both the computer detection score and the neurophysiological detection score.

According to some embodiments of the invention the data processor is configured comparing the computer detection score to the neurophysiological detection score, and re-presenting the image to the observer based on the comparison.

According to some embodiments of the invention the invention the data processor is configured for processing the neurophysiological signals to identify eye blinks, and re-presenting the image to the observer in response to a positive identification of the eye blink during previous presentation of the image.

According to some embodiments of the invention the invention the data processor is configured for repeating the presentation and the identification of the neurophysiological event, comparing the identification to a previous identification of the image, and determining a neurophysiological state of the observer based on the comparison.

According to some embodiments of the invention the invention the data processor is configured for presenting to the observer a database image containing the target, processing the neurophysiological signals to identify a neurophysiological event indicative of a detection of the target in the database image by the observer, and determining a neurophysiological state of the observer based on the identification.

According to some embodiments of the invention the invention the data processor is configured for processing the neurophysiological signals to identify muscle tonus, and re-presenting the image to the observer in response to a positive identification of the muscle tonus during previous presentation of the image.

According to some embodiments of the invention the invention the neurophysiological signals comprise EEG signals, and wherein the data processor is configured for calculating a ratio of slow wave EEG to fast wave EEG and determining a neurophysiological state of the observer based on the ratio.

According to some embodiments of the invention the invention the data processor is configured for processing the neurophysiological signals to identify eye blinks, for evaluating a temporal pattern of the eye blinks, and for determining a neurophysiological state of the observer based on the temporal pattern.

According to some embodiments of the invention the invention the data processor is configured for presenting to the observer a feedback regarding the identification of the neurophysiological event.

According to some embodiments of the invention the system is a virtual reality system.

According to some embodiments of the invention the system is an augmented reality system.

According to an aspect of some embodiments of the present invention there is provided a method of classifying an image. The method comprises: presenting the image to an observer as a visual stimulus, while collecting neurophysiological signals from a brain of the observer; digitizing the neurophysiological signals to provide neurophysiological data; simultaneously processing the image and the neurophysiological data using a convolutional neural network (CNN) to identify a correlation between a computer vision detection of a target in the image and a neurophysiological event indicative of a detection of the target by the observer; and determining an existence of the target in the image based the identified correlation; wherein the CNN comprises a first convolutional neural subnetwork (CNS) configured for receiving and processing the neurophysiological data, a second CNS configured for receiving and processing the image, and a shared subnetwork having a neural network layer receiving and combining outputs from both the first CNS and the second. CNS.

According to some embodiments of the invention the method comprises: assigning to the image a neurophysiological detection score using at least the first CNS; assigning to the image a computer detection score using at least the second CNS; comparing the computer detection score to the neurophysiological detection score; and re-presenting the image to the observer based on the comparison.

According to some embodiments of the invention the method comprises processing the neurophysiological signals to identify eye blinks, and re-presenting the image to the observer in response to a positive identification of the eye blink during previous presentation of the image.

According to some embodiments of the invention the method comprises repeating the presentation and the simultaneous processing, comparing the identification to a previous identification of the image, and determining a neurophysiological state of the observer based on the comparison.

According to some embodiments of the invention the invention the neurophysiological signals comprise EEG signals, and wherein the method comprises calculating a ratio of slow wave EEG to fast wave EEG and determining a neurophysiological state of the observer based on the ratio.

According to some embodiments of the invention the invention the method comprises presenting to the observer a database image containing the target, processing the neurophysiological signals to identify a neurophysiological event indicative of a detection of the target in the database image by the observer, and determining a neurophysiological state of the observer based on the identification.

According to some embodiments of the invention the invention the method comprises processing the neurophysiological signals to identify muscle tonus, and re-presenting the image to the observer in response to a positive identification of the muscle tonus during previous presentation of the image.

According to some embodiments of the invention the invention the neurophysiological signals comprise EEG signals, and wherein the method comprises calculating a ratio of slow wave EEG to fast wave EEG and determining a neurophysiological state of the observer based on the ratio.

According to some embodiments of the invention the invention the method comprises processing the neurophysiological signals to identify eye blinks, evaluating a temporal pattern of the eye blinks and determining a neurophysiological state of the observer based on the temporal pattern.

According to some embodiments of the invention the invention the collecting the neurophysiological signals is at a sampling rate of at least 150 Hz.

According to some embodiments of the invention the invention the method comprises applying a low pass filter to the collected neurophysiological signals.

According to some embodiments of the invention the invention the method comprises presenting to the observer a feedback regarding the identification of the neurophysiological event.

According to some embodiments of the invention the invention the method is used in a virtual reality system.

According to some embodiments of the invention the invention the method is used in an augmented reality system.

According to some embodiments of the invention the invention the method comprises varying a field-of-view provided by the virtual reality or augmented reality system, in response to the determination of the existence.

According to an aspect of some embodiments of the present invention there is provided a system of classifying an image. The system comprises: a data processor configured for receiving the image; a display communicating with the data processor, wherein the data processor is configured for presenting the image to an observer as a visual stimulus; a neurophysiological signal collection system, communicating with the data processor and being configured for collecting neurophysiological signals from a brain of the observer during the presentation and transmitting the signals to the data processor; wherein the data processor is configured for: digitizing the neurophysiological signals to provide neurophysiological data; simultaneously processing the image and the neurophysiological data using a convolutional neural network (CNN) to identify a correlation between a computer vision detection of a target in the image and a neurophysiological event indicative of a detection of the target by the observer, the CNN comprises a first convolutional neural subnetwork (CNS) configured for receiving and processing the neurophysiological data, a second CNS configured for receiving and processing the image data, and a shared subnetwork having a neural network layer receiving and combining outputs from both the first CNS and the second CNS; and determining an existence of the target in the image based the identified correlation.

According to some embodiments of the invention the data processor is configured for: assigning to the image a neurophysiological detection score using at least the first CNS; assigning to the image a computer detection score using at least the second CNS; comparing the computer detection score to the neurophysiological detection score; and re-presenting the image to the observer based on the comparison.

According to some embodiments of the invention the invention the data processor is configured for processing the neurophysiological signals to identify eye blinks, and re-presenting the image to the observer in response to a positive identification of the eye blink during previous presentation of the image.

According to some embodiments of the invention the invention the data processor is configured for repeating the presentation and the simultaneous processing, comparing the identification to a previous identification of the image, and determining a neurophysiological state of the observer based on the comparison.

According to some embodiments of the invention the invention the data processor is configured for presenting to the observer a database image containing the target, processing the neurophysiological signals to identify a neurophysiological event indicative of a detection of the target in the database image by the observer, and determining a neurophysiological state of the observer based on the identification.

According to some embodiments of the invention the invention the data processor is configured for processing the neurophysiological signals to identify muscle tonus, and re-presenting the image to the observer in response to a positive identification of the muscle tonus during previous presentation of the image.

According to some embodiments of the invention the invention the neurophysiological signals comprise EEG signals, and wherein the data processor is configured for calculating a ratio of slow wave EEG to fast wave EEG and determining a neurophysiological state of the observer based on the ratio.

According to some embodiments of the invention the invention the data processor is configured for processing the neurophysiological signals to identify eye blinks, for evaluating a temporal pattern of the eye blinks, and for determining a neurophysiological state of the observer based on the temporal pattern.

According to some embodiments of the invention the invention the data processor is configured for presenting to the observer a feedback regarding the identification of the neurophysiological event.

According to some embodiments of the invention the feedback is binary.

According to some embodiments of the invention the feedback is non-binary.

According to some embodiments of the invention the invention the system is a virtual reality system.

According to some embodiments of the invention the invention the system is an augmented reality system.

According to some embodiments of the invention the invention the data processor is configured for varying a field-of-view provided by the virtual reality or augmented reality system, in response to the determination of the existence.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A, 1B and 1C are block diagrams describing a prototype image classification system, according to some embodiments of the present invention;

FIGS. 2A and 2B show examples descriptors extracted from aerial image of river with objects, according to some embodiments of the present invention;

FIGS. 3A and 3B show detected regions of interest in aerial image of river with objects, as obtained in experiments performed according to some embodiments of the present invention;

FIG. 4 is a schematic illustration of a convolutional neural network, according to some embodiments of the present invention;

FIG. 5 is a graph showing true positive rate (TPR) as a function of false negative rate (FPR), as Obtained according to some embodiments of the present invention using a combination of classifiers;

FIG. 6 is a flowchart diagram describing an operation principle of an analysis module according to some embodiments of the present invention;

FIG. 7 is a screenshot of a display of the prototype image classification system, according to some embodiments of the present invention;

FIG. 8 is another screenshot of a display of the prototype image classification system, according to some embodiments of the present invention;

FIG. 9A shows an average brain response (ERP) to targets and non-targets at one EEG electrodes, as obtained in experiments performed according to some embodiments of the present invention for X ray images;

FIG. 9B shows a distribution of electrical potentials on the head of an observer, as obtained in experiments performed according to some embodiments of the present invention for X ray images;

FIGS. 10A and 10B show a difference between brain responses to single images of Targets and Non-Targets, as measured in experiments performed according to some embodiments of the present invention for X ray images;

Figure 11:
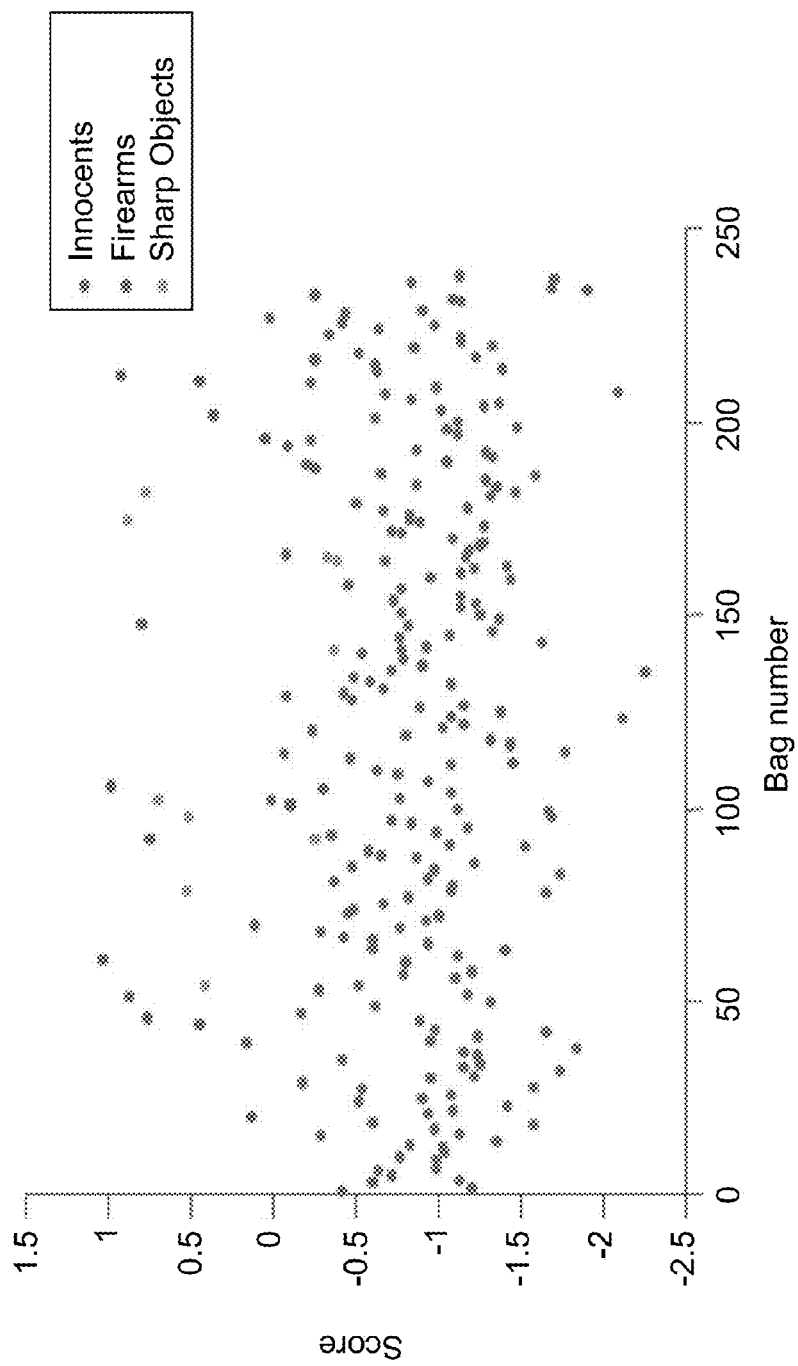
Figure 12:
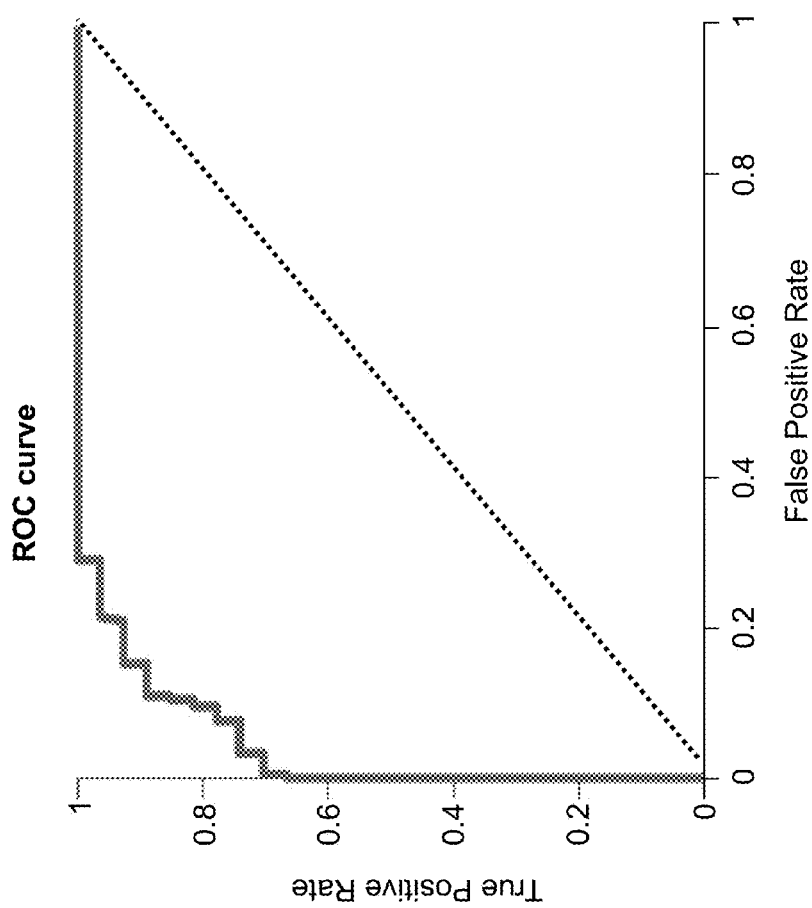
Figure 13:
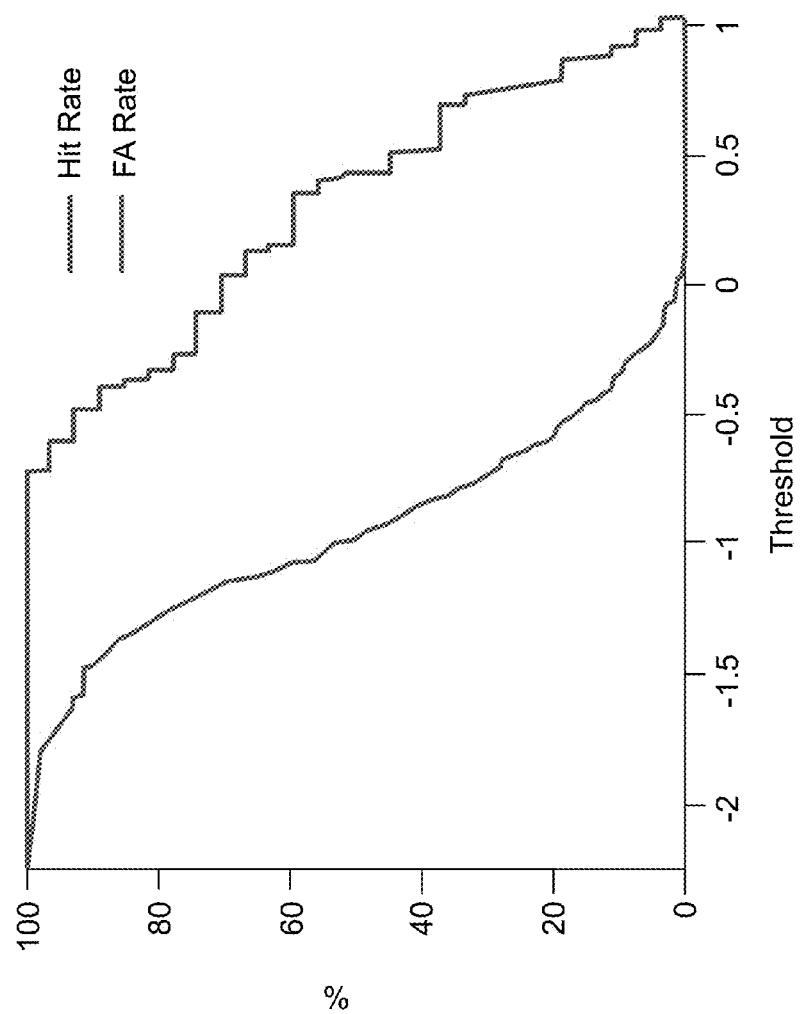
Figures 14A, 14B:
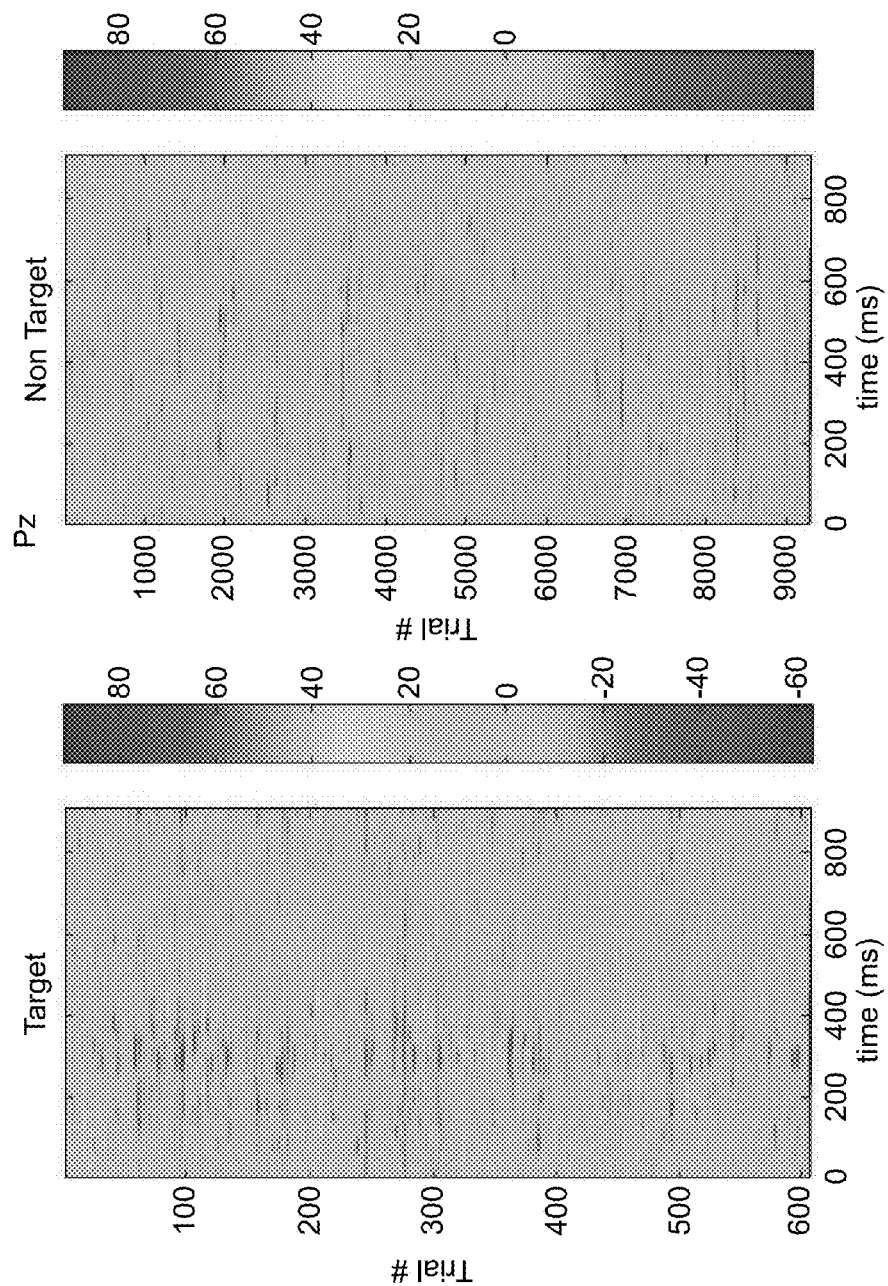
Figure 15:
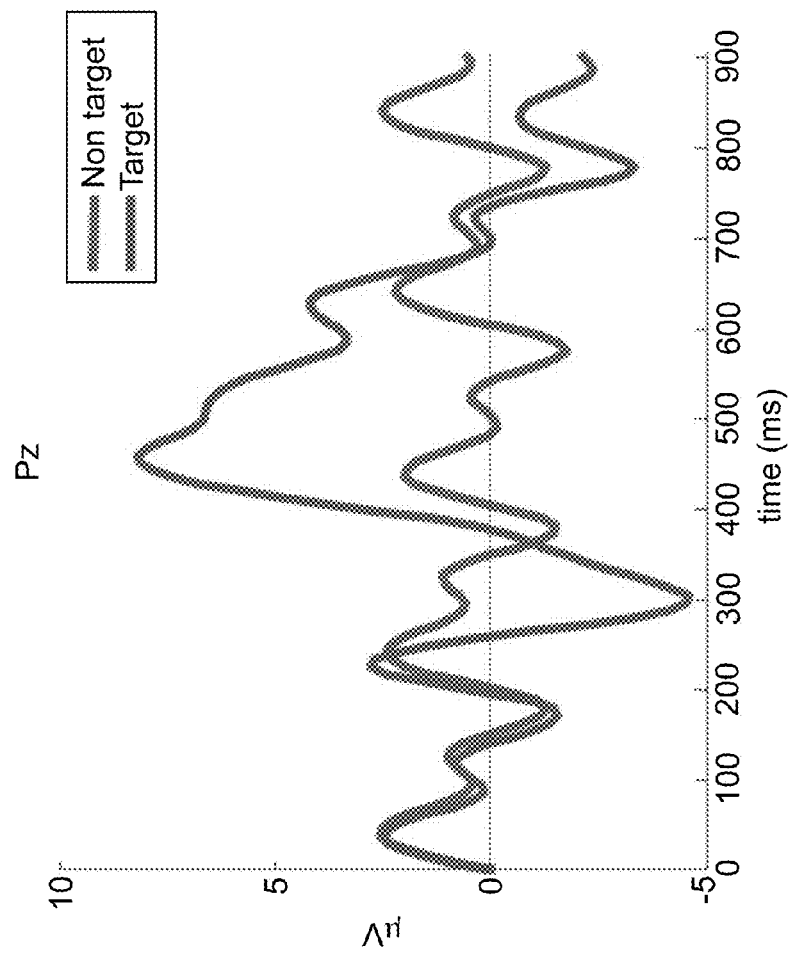
Figure 16:
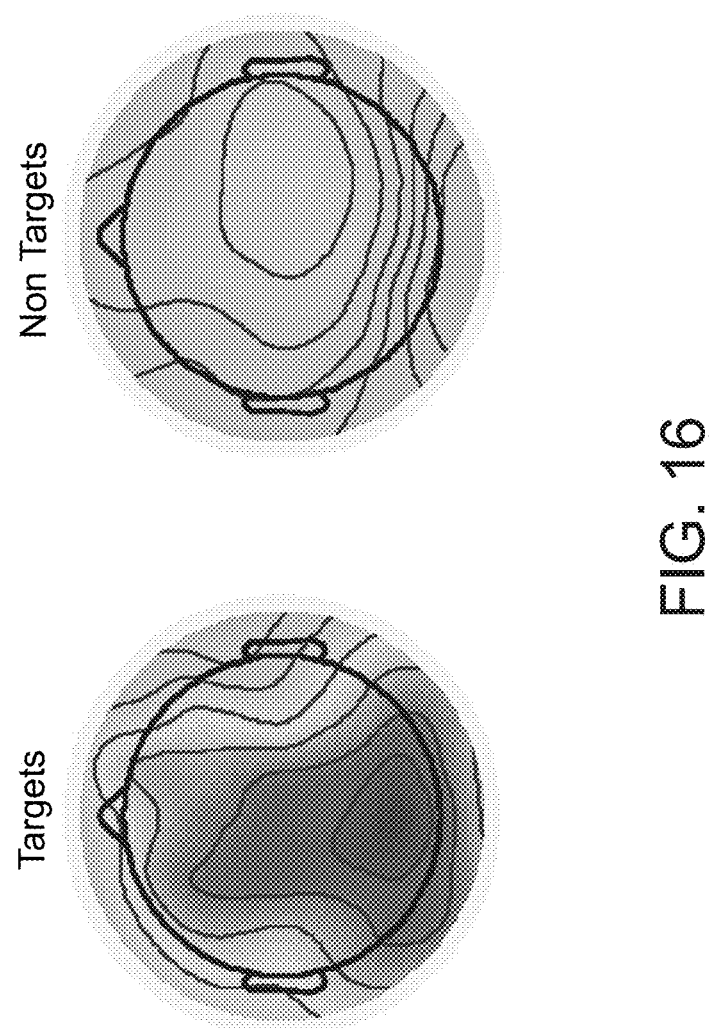
Figure 17:
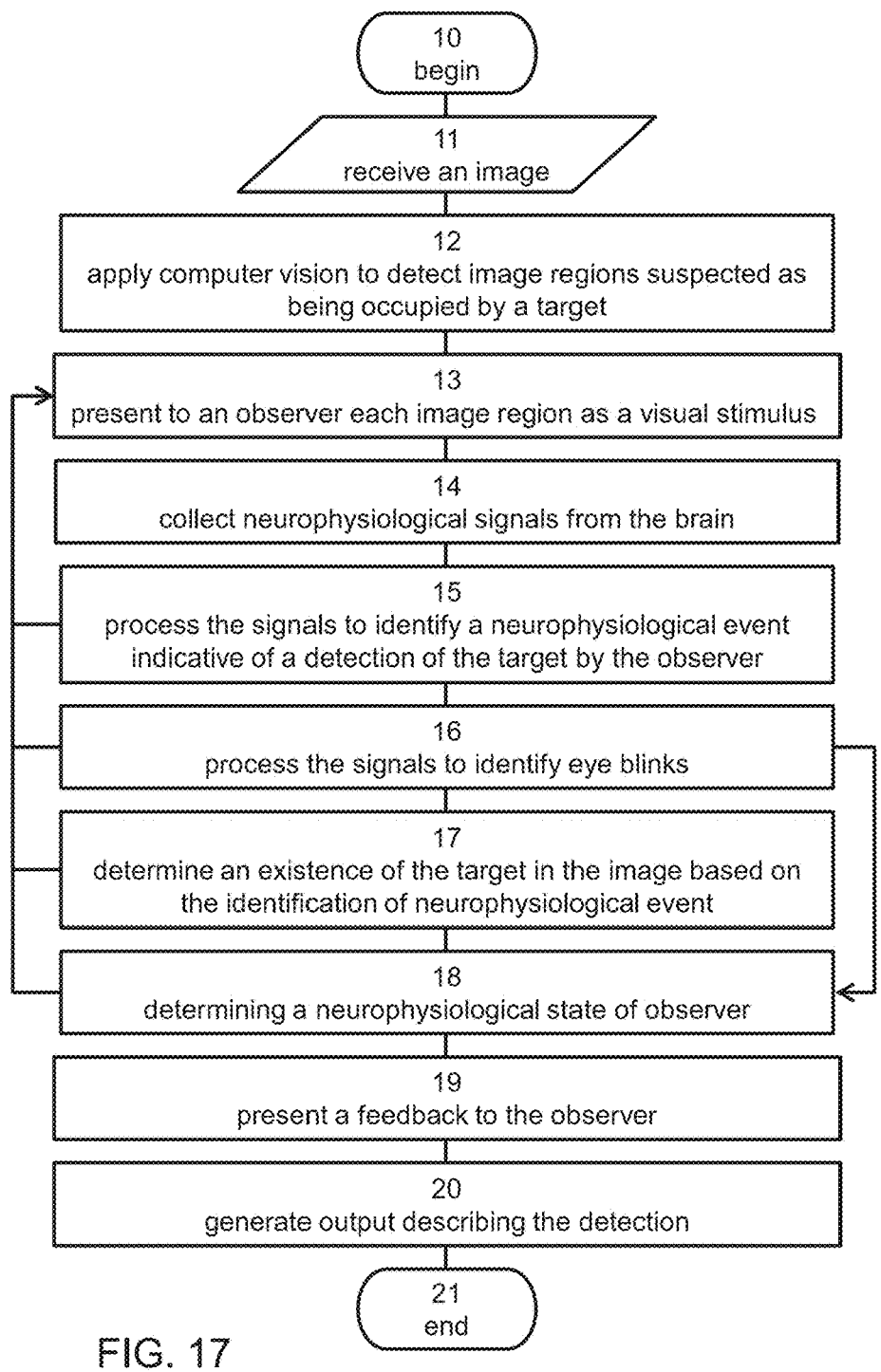
Figure 18:
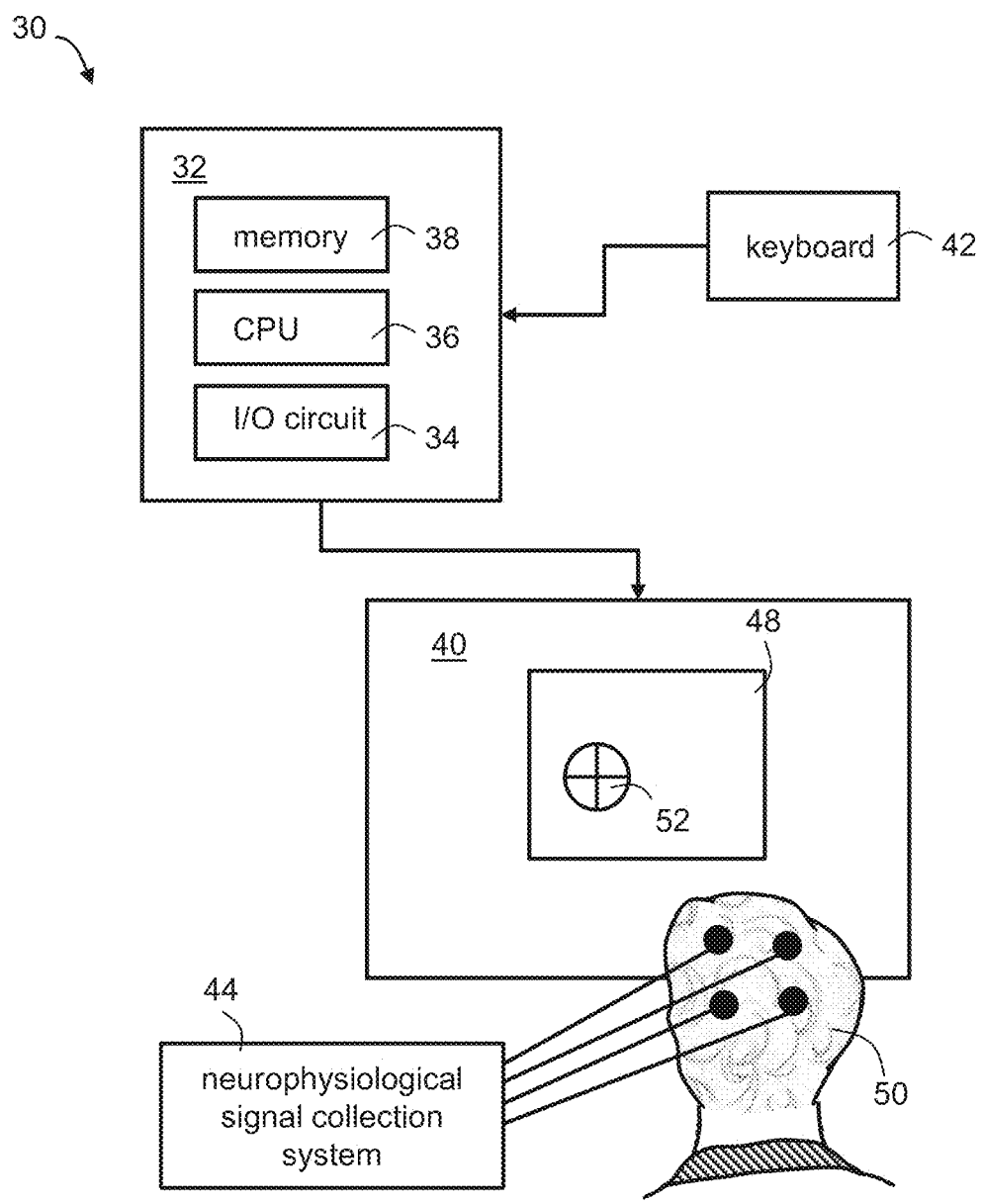
Figure 19:
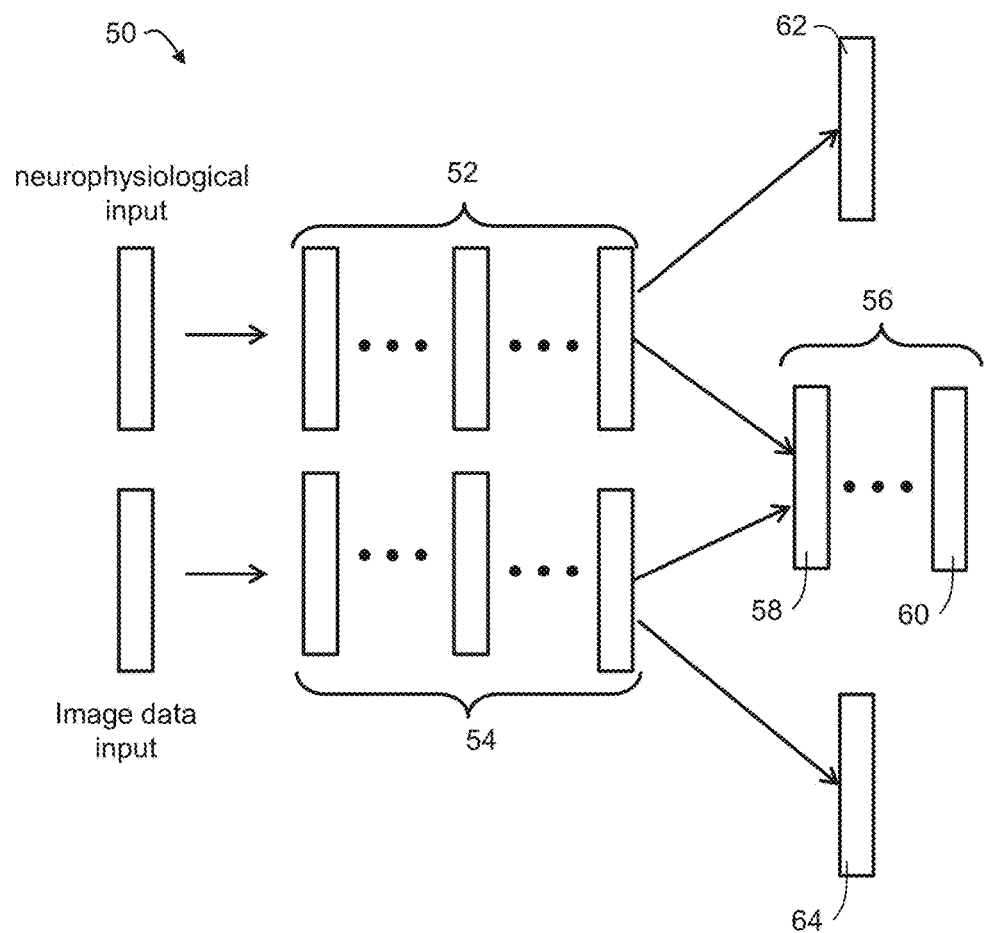

FIG. 11 shows scores distribution of a test phase dataset, used in experiments performed according to some embodiments of the present invention for X ray images;

FIG. 12 shows a Receiver Operating Characteristic (ROC) curve illustrating a performance of a classifier used in experiments performed according to some embodiments of the present invention at different thresholds for X ray images;

FIG. 13 shows hit rates and false alarm (FA) rates as obtained in experiments performed according to some embodiments of the present invention for X ray images;

FIGS. 14A and 14B show a difference between brain responses to single images of targets and non-targets as obtained in experiments performed according to some embodiments of the present invention for aerial images;

FIG. 15 shows average brain response (ERP) to targets and non-targets at one electrodes as obtained in experiments performed according to some embodiments of the present invention for aerial images;

FIG. 16 shows a distribution of electrical potentials on the head of an observer as obtained in experiments performed according to some embodiments of the present invention for aerial images;

FIG. 17 is a flowchart diagram of a method suitable for classifying an image, according to various exemplary embodiments of the present invention;

FIG. 18 is a schematic illustration of a system for classifying an image, according to some embodiments of the present invention; and FIG. 19 is schematic illustration of a multimodal convolutional neural network, according to some embodiments of the present invention.

DESCRIPTION OF SPECIFIC EMBODIMENTS OF THE INVENTION

The present invention, in some embodiments thereof, relates to a Brain Computer Interface and, more particularly, but not exclusively, to a method and system for classification of an image.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Embodiments of the present invention are directed to a method suitable for classifying an image, more preferably within a stream of images, even more preferably each image in stream of images, by BCI. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

At least part of the operations can be can be implemented by a data processing system, e.g., a dedicated circuitry or a general purpose computer, configured for receiving data and executing the operations described below. At least part of the operations can be implemented by a cloud-computing facility at a remote location. The data processing system or cloud-computing facility can serve, at least for part of the operations as an image processing system, wherein the data received by the data processing system or cloud-computing facility include image data.

Computer programs implementing the method of the present embodiments can commonly be distributed to users on a distribution medium such as, but not limited to, a floppy disk, a CD-ROM, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

Reference is now made to FIG. 17 which is a flowchart diagram of a method suitable for classifying an image, according to various exemplary embodiments of the present invention.

The method begins at 10 and continues to 11 at which an image is received, the image can be of any type, including, without limitation, a color image, an infrared image, a ultraviolet image, a thermal image, a grayscale image, a high dynamic range (HDR) image, an aerial image, a medical image, a satellite image, an astronomy image, a microscope image, an MRI image, an X-ray image, a thermal image, a computerized tomography (CT) image, a mammography image, a positron emission tomography (PET) image, an ultrasound image, an impedance image, and a single photon emission computed tomography (SPECT) image.

The method continues to 12 at which a computer vision procedure is applied to the image to detect therein image regions suspected as being occupied by a target. This operation results in a set of candidate image regions. The target can be provided as input to the method, or more preferably to an image processor that executes the computer vision procedure. The input can be in the form of a reference image or as a set of one or more computer readable descriptors that allows the image processor to determine whether or not the target occupies a region in the image. The target can be any visible object of any shape, including living objects (humans or animals), organs of living objects (e.g., faces, limbs), inanimate objects, and parts of inanimate objects.

The set provided at 12 can include any number of image regions, including a single image region. It is appreciated that there are cases in which a computer vision procedure fails to detect a target in an image. In these cases, the set provided at 12 is the null set.

The present embodiments contemplate any type of computer vision procedure suitable for detecting input targets in an image. One preferred computer vision procedure is known as "bag of visual words" or "bag of keypoints," found, for example, in Ref. [1]. This procedure makes use of a "visual dictionary" also known as "visual vocabulary" to provide a mid-level characterization of images for bridging the semantic gap between low-level features and high-level concepts. The visual dictionary can be estimated in an unsupervised manner by clustering a set of training samples, which can be low level features extracted from training images. Each of at least a portion of the feature vectors of the image is assigned to its closest cluster, and an occupancy histogram is built. The image can then be classified by providing the occupancy histogram to a set of classifiers (one per class). Representative examples classifiers suitable for use in a computer vision procedure employed according to some embodiments of the present invention including, without limitation, Support Vector Machine (SVM), Adaptive Boosting, Naive Bayes, and the like.

In the bag of keypoints procedure, keypoints in the image can be detected, for example, using a Speeded up Robust Features (SURF) detector to form a feature vector. A supervised or, more preferably, unsupervised cluster analysis can then be applied to the feature vectors, to construct the dictionary of visual words. Representative example of clustering analysis procedure suitable for the present embodiments including, without limitation, (e.g., k-Means, fuzzy K-means, hierarchical clustering and Bayesian clustering.

Also contemplated are computer vision procedures employing unsupervised neural network. One such preferred computer vision procedure relates to sparse autoencoder. In this case, patches of the image are extracted, optionally and preferably randomly, from the image, and each patch is concatenated to form a column vector. Each vector is optionally and preferably passed through a neural network, typically, but not necessarily a two-layer neural network, to provide a set of filters. The image can be filtered by convolution with these filters to obtain a set of filtered images, which can be used to form a feature vector.

The present embodiments also contemplate use of more than one type of computer vision procedure to detect the image regions. For example, at 12 a collection of image regions obtained by applying two or more different types of computer vision procedure can be obtained. A more detailed description of computer vision procedures suitable for the present embodiments is provided in the Examples section that follows.

In some embodiments of the present invention the computer vision procedure is also used for assigning a computer detection score to the image at 12. For example, the score can be at the range [0, 1] wherein 0 corresponds to an image for which the computer vision procedure failed to detect the target, 1 corresponds to an image for which the computer vision procedure detected the target.

The method continues to 13 at which each candidate image region is presented to an observer (preferably human observer) as a visual stimulus. This can be done using a display device. In some embodiments the image is tiled into a plurality of image tiles, such that at least one tile encompasses a candidate image region. In these embodiments, tiles that encompass candidate image regions are presented at 13. The advantage of these embodiments is that the size (e.g., area) of the tiles can be selected to ease the visual perception of the observer.

Alternatively, the entire image can be presented to the observer, rather than only candidate image regions. The image can be presented as a whole, or be tiled into a plurality of image tiles, that may or may not encompass a candidate image region. In these embodiments, the image or a tile of the image is presented at 13 irrespectively whether or not it encompasses a candidate region.

The regions, or tiles, are preferably presented serially at a sufficiently high rate. Such presentation is referred to as Rapid Serial Visual Presentation (RSVP). The rate is preferably selected so that it can cope with overlapping responses in a rapid series of visual presentation. Representative presentation rates suitable for the present embodiments are from about 2 Hz to about 20 Hz or from about 2 Hz to about 15 Hz or from about 2 Hz to about 10 Hz or from about 5 Hz to about 20 Hz or from about 5 Hz to about 15 Hz or from about 5 Hz to about 10 Hz.

The method continues to 14 at which neurophysiological signals are collected from a brain of the observer. Operation 14 is preferably executed contemporaneously with the visual stimulus 13, so that the collected signals include also signals that are indicative of the Observer's response to the visual stimulus. The neurophysiological signals are preferably encephalogram (EG) signals, such as electroencephalogram (EEG) signals or magnetoencephalogram (MEG) signals. Other types of signals are also contemplated, but the present inventors found that EEG signals are preferred.

The EEG signals are preferably collected, optionally and preferably simultaneously, from a multiplicity of electrodes (e.g., at least 4 or at least 16 or at least 32 or at least 64 electrodes), and optionally and preferably at a sufficiently high temporal resolution. In some embodiments of the present invention signals are sampled at a sampling rate of at least 150 Hz or at least 200 Hz or at least 250 Hz, e.g., about 256 Hz. Optionally, a low-pass filter of is employed to prevent aliasing of high frequencies. A typical cutoff frequency for the low pass filter is, without limitation, about 51 Hz.

When the neurophysiological signals are EEG signals, one or more of the following frequency bands can be defined: delta band (typically from about 1 Hz to about 4 Hz), theta band (typically from about 3 to about 8 Hz), alpha band (typically from about 7 to about 13 Hz), low beta band (typically from about 12 to about 18 Hz), beta band (typically from about 17 to about 23 Hz), and high beta band (typically from about 22 to about 30 Hz). Higher frequency bands, such as, but not limited to, gamma band (typically from about 30 to about 80 Hz), are also contemplated.

Electrodes can be placed at one or more, optionally and preferably all, of the following locations: two on the mastoid processes, two horizontal EOG channels positioned at the outer canthi of the left and right eyes, two vertical EOG channels, one below and one above the right eye, and a channel on the tip of the nose.

The method continues to 15 at which the neurophysiological signals are processed to identify a neurophysiological event indicative of a detection of the target by the observer. According to some embodiments, the observer is provided with a priori knowledge regarding the target that is to be identified in the image. For example, a region-of-interest including the target can be displayed to the observer, and the observer can be asked to memorize the target in the displayed region-of-interest.

The processing 15 can be done in more than one way. Following is a description of several techniques that can be used for identifying a neurophysiological event in the neurophysiological signals.

The processing typically includes a digitization procedure that generates digital data from the signals. These data are typically arranged as a spatiotemporal matrix, in which the spatial dimension corresponds to electrode location on the scalp of the observer, and the temporal dimension is a discretization of the time axis into a plurality of time points or epochs, that may or may not be overlapped. The data can then be subjected to a dimensionality reduction procedure for mapping the data onto a lower dimensional space. The processing may optionally, but not necessarily, be based on frequency-bands relevant to target detection. Specifically, the processing may be primarily based on the P300 EEG wave.

The processing is preferably automatic and can be based on supervised or unsupervised learning from training data sets. Learning techniques that are useful for identifying a target detection events include, without limitation, Common Spatial Patterns (CSP), autoregressive models (AR) and Principal Component Analysis (PCA). CSP extracts spatial weights to discriminate between two classes, by maximizing the variance of one class while minimizing the variance of the second class. AR instead focuses on temporal, rather than spatial, correlations in a signal that may contain discriminative information. Discriminative AR coefficients can be selected using a linear classifier.

PCA is particularly useful for unsupervised learning. PCA maps the data onto a new, typically uncorrelated space, where the axes are ordered by the variance of the projected data samples along the axes, and only axes that reflect most of the variance are maintained. The result is a new representation of the data that retains maximal information about the original data yet provides effective dimensionality reduction.

Another method useful for identifying a target detection event employs spatial Independent Component Analysis (ICA) to extract a set of spatial weights and obtain maximally independent spatial-temporal sources. A parallel ICA stage is performed in the frequency domain to learn spectral weights for independent time-frequency components. PCA can be used separately on the spatial and spectral sources to reduce the dimensionality of the data. Each feature set can be classified separately using Fisher Linear Discriminants (FLD) and can then optionally and preferably be combined using naive Bayes fusion, by multiplication of posterior probabilities).

Another technique employs a bilinear spatial-temporal projection of event-related data on both temporal and spatial axes. These projections can be implemented in many ways. The spatial projection can be implemented, for example, as a linear transformation of signals into underlying source space or as ICA. The temporal projection can serve as a filter. The dual projections can be implemented on non-overlapping time windows of the single-trial data matrix, resulting in a scalar representing a score per window. The windows' scores can be summed or classified to provide a classification score for the entire single trial. In addition to the choice of this technique can support additional constraints on the structure of the projections matrix. One option is, for example, to learn the optimal time window for each channel separately and then train the spatial terms.

In various exemplary embodiments of the invention the method employs a Spatially Weighted Fisher Linear Discriminant (SWFLD) classifier to the neurophysiological signals. This classifier can be obtained by executing at least some of the following operations. Time points can be classified independently to compute a spatiotemporal matrix of discriminating weights. This matrix can then be used for amplifying the original spatiotemporal matrix by the discriminating weights at each spatiotemporal point, thereby providing a spatially-weighted matrix.

Preferably the SWFLD is supplemented by PCA. In these embodiments, PCA is optionally and preferably applied on the temporal domain, separately and independently for each spatial channel. This represents the time series data as a linear combination of components. PCA is optionally and preferably also applied independently on each row vector of the spatially weighted matrix. These two separate applications of PCA provide a projection matrix, which can be used to reduce the dimensions of each channel, thereby providing a data matrix of reduced dimensionality.

The rows of this matrix of reduced dimensionality can then be concatenated to provide a feature representation vector, representing the temporally approximated, spatially weighted activity of the signal. An FLD classifier can then be trained on the feature vectors to classify the spatiotemporal matrices into one of two classes. In the present embodiments, one class corresponds to a target identification event, and another class corresponds to other events. More details regarding the SWFLD classifier according to some embodiments of the present invention is provided in the Examples section that follows.

In various exemplary embodiments of the invention the method employs a convolutional neural network (CNN) classifier to the neurophysiological signals. In these embodiments the CNN receives the signals as a spatiotemporal matrix and produces a score, typically in the range [0, 1] which estimates the probability that the presented visual stimulus is a target. The network can optionally and preferably be trained using stochastic gradient descent (SGD) to minimize a logistic regression cost function. In a preferred embodiment the CNN comprises a first convolution layer applying spatial filtering for each of a plurality of time points characterizing the neurophysiological signals, a second convolution layer applying temporal filtering to outputs provided by the first convolution layer, and optionally and preferably also a third convolution layer applying temporal filtering to outputs provided by the second convolution layer. The second and third convolution layers typically learn temporal patterns in the signal that represent the change in amplitude of the spatial maps learned by the first layer, and therefore advantageous since they improve the classification accuracy.

The CNN can also comprise two or more fully connected layers each providing a non-linear combination of the outputs provided by a layer preceding the respective fully connected layer. A first fully connected layer preferably receives output from the third convolutional layer (when a third convolutional layer is employed) or the second convolutional layer (preferably, but not necessarily, when a third convolutional layer is not employed). A second fully connected layer preferably receives output from the first from the first fully connected layer. Optionally, the CNN comprises two or more pooling layers, e.g., max-pooling layers, to reduce dimensionality. More details regarding the preferred CNN is provided in the Examples section that follows.

The processing 15 optionally and preferably comprises calculating a score describing the probability that a target exists in the image. The score is calculated using the respective classifier. For example, when the classifier is an SWFLD classifier, a Fisher score can be calculated, and when the classifier is a CNN classifier, the score can be the output of the logistic regression layer of the CNN.

In a preferred embodiment, the method employs an observer-specific score normalization function for normalizing the calculated score. Such an observer-specific score normalization function is typically prepared at a training stage in which the method is repeatedly executed for the same observer using a training dataset of images, wherein each image of the dataset is classified as either containing or not containing the target. The observer-specific score normalization function can also be target specific, in which case the training stage is repeated for each target to be detected. However, this need not necessarily be the case, since, for some applications, it may not be necessary to repeat the training for each target, since the observer's ability to detect different targets may be similar, particularly when the different targets belong to the same category (e.g., different vehicles, different faces, etc.).

During the training stage, a first score distribution function is calculated for target classified as containing the target, and a second score distribution function is calculated for target classified as not containing the target. The score distribution functions that are calculated at the training stage, then used to normalize the score provided at the running stage. For example, denoting the first score distribution function by $g_1$, and the second score distribution function by $g_0$, a score s provided by the classifier at the running stage can be normalized to provide a normalized score $\tilde{s}$ defined as $\tilde{s}=g_1(s)/(g_0(s)+g_1(s))$.

The first and second score distribution functions can have a predetermined shape in the score space. Typically the shape is localized. Representative examples of types of distribution functions suitable for use as first and second score distribution functions including, without limitation, a Gaussian, a Lorenzian and a modified Bessel function.

The normalized score can be compared to a predetermined confidence threshold to determine the level of confidence of the identified detection event. When the normalized is below the predetermined confidence threshold, the method optionally and preferably loops back to 13 to re-present the respective image region or group of image regions to the observer and re-calculate the normalized score.

In some embodiments, two different types of classifiers are used and a score that weighs the scores provided by the individual classifiers is computed. For example, the method can apply an SWFLD classifier and calculate a SWFLD classification score based on the SWFLD classifier, applies a CNN classifier and calculate a CNN classification score based on the CNN classifier, and combines the SWFLD score and the CNN score. The combination of the two score may optionally and preferably be preceded by a score resealing operation that brings the two scores to similar scale. The aforementioned normalization using the first and second score distribution functions can also serve for resealing the scores.

In some embodiments of the present invention the method proceeds to 16 at which the neurophysiological signals are processed to identify eye blinks. In these embodiments, when there is a positive identification of an eye blink during a presentation of an image region or group of image regions to the observer, the method optionally and preferably loops back to 13 and re-presents the respective image region or group of image regions to the observer. Eye blinks can be identified using any technique known in the art, such as the technique disclosed in U.S. Pat. No. 5,513,649 and U.S. Published Application No. 20150018704, the contents of which are hereby incorporated by reference.

The method proceeds to 17 at which an existence of target in the image is determined based, at least in part, on the identification of the neurophysiological event. For example, the method determines that the target exists in the image when a detection event has been identified in one or more of the regions presented in 13. Optionally, a neurophysiological detection score is assigned to the image (or an image region, is only a region is presented at a given time, or an image tile if only an image tile is presented at a given time), for example, using the score generated by the classifier at 15 or using a combined score if more than one classifier is employed. When neurophysiological detection score is assigned to the image, the determination 17 is preferably based, at least in part, on the neurophysiological detection score. This can be done, for example, by thresholding, wherein when the neurophysiological detection score is above a predetermined threshold the method determines that the target is in the image, and when the neurophysiological detection score is not above the predetermined threshold the method determines that the target is not in the image. The method can also assign a probability value to the existence of the target in the image. This can be done based on the neurophysiological detection score. For example, the score can be mapped into a probabilistic scale (e.g., in the range [0,1]) and the value of the mapped score can be used as a target existence probability.

When a computer detection score is assigned to the image using computer vision procedure, the determination 17 is preferably based on both the computer detection score and the neurophysiological detection score. For example, when both scores are high, the method can determine that the target exists in the image. When the scores mismatch (for example, when the computer detection score is high but the neurophysiological detection score is low), the method optionally and preferably loops back to 13 and re-presents the respective image region or group of image regions to the observer.

The present embodiments also contemplate the use of a multimodal CNN for simultaneously processing the image data that form the image and the neurophysiological data that describes the response of the observer to the presentation of the image (or image region or image tile). The multimodal CNN can be used to identify a correlation between the computer vision detection and the neurophysiological detection, in a manner that will now be explained with reference to FIG. 19.

Shown in FIG. 19 is a multimodal CNN 50 which comprises a first convolutional neural subnetwork (CNS) 52 that receives and processes neurophysiological data obtained by digitizing the signals collected at 14, and a second CNS 52 that receives and processes the image data received at 11. In various exemplary embodiments of the invention each of first CNS 52 and second. CNS 54 operates independently, in a manner that each of subnetworks 52 and 54 receives and processes a different type of data (neurophysiological data for the CNS 52, and image data for CNS 54), and there is no data flow between subnetworks 52 and 54. Thus, in these embodiments, the input layer of CNS 52 receives neurophysiological data but not image data, the input layer of CNS 54 receives image data but not neurophysiological data, each layer of CNS 52 (other than its input layer) receives data from a layer of CNS 52 that proceeds the respective layer but not from any layer of CNS 54, and each layer of CNS 54 (other than its input layer) receives data from a layer of CNS 54 that proceeds the respective layer but not from any layer of CNS 52.

A least a portion of CNS 52 can be configured as described above with respect to the classification of the neurophysiological signals. At least a portion of CNS 54 can be configured as described above with respect to the computer vision procedure.

CNN 50 also comprises a shared subnetwork 56 having a neural network layer 58 receiving and combining outputs from both CNS 52 and CNS 54. Typically, the output of each of CNS 52 and CNS 54 is a one-dimensional vector. In these embodiments, layer 58 can be a concatenation layer that concatenates the output vector provided by CNS 52 with the output vector provided by CNS 54. Shared subnetwork 56 can also comprise an output layer 60 that calculates a score using the concatenated vector provided by layer 58. It was found by the inventors of the present invention that such a score describes the correlation between the between the computer vision detection and the neurophysiological detection, in a manner that. Layer 60 can calculate the score using any technique known in the art, including, without limitation, a softmax activation function or a logistic regression function.

While CNN 50 combines the output of CNS 52 and CNS 54 it was found by the inventors of the present invention that it is also beneficial to split the output of at last one of these convolutional subnetworks such that the respective output are combined by shared subnetwork 56 but are also processed separately. This can be done by means of an additional neural network layer or an additional subnetwork that receives the output of the respective CNN but not the other CNN. Shown in FIG. 19 is a first additional neural network layer 62 that receives the output of CNS 52 and a second additional neural network layer 64 that receives the output of CNS 54. Each of the additional layers 62 and 64 can separately calculate a score using the output vector of the respective CNS.

The advantage of these embodiments is that they allow distinguishing between the accuracy of the neurophysiological and computer vision detections. For example, the method can assign to the image a neurophysiological detection score as calculated by layer 62, assigning to the image a computer detection score as calculated by layer 64, compare the computer detection score to the neurophysiological detection score; and re-presenting the image to observer based on the comparison, as further detailed hereinabove.

Another advantage of the split of output is that it allows presenting the observer only an image or a region or a tile that in which a computer vision detection occurred. For example, operation 12 described above can be executed by CNS 54 and layer 64.

It is appreciated that it is not necessary to split the outputs of CNS 52 and CNS 54. A separate score for the neurophysiological detection and for the computer detection can be obtained by applying any of the above procedures for processing neurophysiological signals and/or computer vision procedures in addition to the application of CNN 50.

The method optionally and preferably continues to 18 at which the neurophysiological state of observer is determined. This can be done in more than one way.

In some embodiments of the present invention the presentation 13, collection 14 and identification 15 are repeated for one or more image regions. The repeated identification is compared to the previous identification and the neurophysiological state of the observer is determined based on the comparison. For example, when the two identifications do not match, the method can determine that the observer has lost attention or is fatigued. The comparison between the identifications can be either a binary comparison, in which case the method determine whether or not the observer identified the target in both presentation instances, or non-binary in which case the method compares the scores provided by the classifier at 15 in both presentation instances, and determine the neurophysiological state based on the variability (e.g., difference, ratio) of these scores, wherein higher variability indicates an attention loss or fatigue.

In some embodiments of the present invention a ratio of slow wave EEG to fast wave EEG is calculated, and the neurophysiological state of observer is determined a based on this ratio. A representative example of such a ratio is (theta+alpha)/beta, where theta, alpha and beta are magnitude of EEG waves at the respective frequency bands. An increase in this ratio indicates an increase in fatigue levels.

In some embodiments of the present invention a database image region containing the target is presented to the observer. And the collection 14 and processing 15 are repeated for the database image. This is useful for determining a false negative event by the observer. The result of the identification at 15 can be used for determining the neurophysiological state of the observer. For example, when the presentation of database image region at 13 results in a false negative event at 15, the method can determine that the observer has lost attention or is fatigued.

In some embodiments of the present invention the identification of eye blink at 16 can be used for determining the neurophysiological state of the observer. In these embodiments, a temporal pattern of the eye blinks can be evaluated and used for the determining the neurophysiological state. For example, an observer-specific eye blink threshold can be obtained, e.g., from a computer readable memory medium, and compared to the rate of eye blinks. When the rate of eye blinks is above the observer-specific eye blink threshold the method can determine that the observer is fatigued. An observer-specific eye blink threshold can be recorded prior to the execution of the method.

In some embodiments of the present invention muscle tonus is identified and the neurophysiological state of the observer is determined based on the identification of muscle tonus or lack thereof. Muscle tonus can be identified using a specific sensor, such as, but not limited to, the sensor described in U.S. Pat. No. 5,579,783 or U.S. Published Application No. 20110087128, the contents of which are hereby incorporated by reference, or by analyzing the neurophysiological signals.

When an attention loss, fatigue or other condition that reduces the ability of observer to correctly detect the target is identified at 18, the method optionally and preferably loops back to 13 to re-present the respective image region or group of image regions to the observer.

At 19, the method optionally and preferably presents to observer a feedback regarding the identification of neurophysiological event. The feedback serves as a neurofeedback that allows the observer to learn how to change his or hers brain responses to the visual stimuli and to improve the neurophysiological identification. The learning process of the observer can be implicit, such that the observer is not able to explicitly express how the neurophysiological identification is improved. Alternatively, the feedback can be explicit by requiring the observer to provide a cognitive or emotional strategy for improving the identification. The process of providing a feedback can be repeated in an iterative manner, wherein classification parameters of the processing 15 are updated following each accurate identification and inaccurate identifications, and the feedback is re-presented to further improve the neurophysiological identification. It was found by the Inventor that by adapting the brain responses to improve the neurophysiological identification, the image interpretation skills of the observer are improved, since the observer implicitly learns how the signal processing 15 identifies detection event.

The feedback can be a binary feedback, e.g., one of a positive feedback for a correct identification (true positive or true negative), and negative feedback for incorrect identification (false positive or false negative). Alternatively, the feedback can be non-binary, e.g., a feedback that presents the score calculated at 15. The feedback can be provided visually, audibly, or tactilely, as desired.

At 20, an output describing the identification is generated. This can be done in more than one way. In some embodiments of the present invention the output is in the form of a collection (an album) of images, wherein each image in the album is associated with a detection score (e.g., a neurophysiological detection score, or a combined score as described above). In some embodiments of the present invention only images whose scores exceed a score threshold are included in the album. The score threshold can be predetermined or dynamically updated.

In some embodiments of the present invention the output is in the form of a map including more than one image classified by the observer. In these embodiments the image is segmented into a plurality of tiles, optionally and preferably with an overlap between adjacent tiles in both the vertical and horizontal directions. The overlap is optionally and preferably such that a fraction p of the tile is shared with the adjacent tile, where the fraction p is larger than some fraction threshold (e.g., p>0.5, but other values for the fraction threshold are also contemplated). The map can be embodied as a matrix such that each matrix-element of the matrix corresponds to an nth of a tile. A score is optionally and preferably calculated for each nth of a tile. For example, the score can be the average of the neurophysiological detection scores or combined scores of all the tiles that contain the respective nth of the tile. Once the matrix is computed, it can be displayed as an image with points with higher scores being marked as potential targets. Such a map is referred to as a heat map. Additional potential targets can be located by searching for local maxima of the heat map.

The method ends at 21.

The method of the present embodiments can be used for identifying a target a stream of images transmitted to a display observed by the observer from any source. The source can be a computer readable storage medium storing the images, or an imaging system. The method of the present embodiments can also be employed in a virtual reality or an augmented reality system. In these embodiments, the results of the determination at 18 can be used for identifying targets in the field-of-view presented to the user of the virtual reality or an augmented reality system. For example, upon a positive target identification, the virtual reality or an augmented reality system can to vary the field-of-view presented to the user (e.g., shift, zoom in, zoom out, or rotate the displayed image, to create an illusion of motion). This can be done automatically without intervention of a peripheral device such as a joystick or the like. The identified target can be a virtual object displayed by the virtual or augmented reality system. When the method is employed in an augmented reality system the target can be a real object in the scene displayed by the augmented reality system.

Reference is now made to FIG. 18 which is a schematic illustration of a system 30 for classifying an image, according to some embodiments of the present invention. System 30 comprises a data processor 32, a display 40 communicating with data processor 32, and a neurophysiological signal collection system 44. System 30 can be used for executing any of the operations, e.g., all the operations of the method described above. System 30 can be a stationary target identification system, or be, or combined with, a mobile system, such as, but not limited to, a virtual reality system of augmented reality system.

Data processor 32, typically comprises an input/output (I/O) circuit 34, a data processing circuit, such as a central processing unit (CPU) 36 (e.g., a microprocessor), and a memory 46 which typically includes both volatile memory and non-volatile memory. I/O circuit 34 is used to communicate information in appropriately structured form to and from other CPU 36 and other devices or networks external to system 30. CPU 36 is in communication with I/O circuit 34 and memory 38. These elements can be those typically found in most general purpose computers and are known per se.

A display device 40 is shown in communication with data processor 32, typically via 110 circuit 34. Data processor 32 issues to display device 40 graphical and/or textual output images generated by CPU 36. A keyboard 42 is also shown in communication with data processor 32, typically I/O circuit 34.

It will be appreciated by one of ordinary skill in the art that system 30 can be part of a larger system. For example, system 30 can also be in communication with a network, such as connected to a local area network (LAN), the Internet or a cloud computing resource of a cloud computing facility.

Neurophysiological signal collection system 44 optionally and preferably communicates with data processor 32 and is configured for collecting neurophysiological signals from a brain of an observer as further detailed hereinabove.

In some embodiments of the invention data processor 32 of system 30 is configured for applying a computer vision procedure to the image to detect therein image regions suspected as being occupied by the target, thereby providing a set of candidate image regions, for presenting to an observer 50, by display 40, each candidate image region 48 as a visual stimulus, for processing the neurophysiological signals received from system 36 to identify a neurophysiological event indicative of a detection of a target 52 by observer 50, and for determining an existence of target 52 in the image based, at least in part, on the identification of the neurophysiological event, as further detailed hereinabove.

In some embodiments of the invention system 30 communicates with a cloud computing resource (not shown) of a cloud computing facility, wherein the cloud computing resource is configured for applying a computer vision procedure to the image to detect therein image regions suspected as being occupied by the target, thereby providing a set of candidate image regions, for presenting to an observer 50, by display 40, each candidate image region 48 as a visual stimulus, for processing the neurophysiological signals received from system 36 to identify a neurophysiological event indicative of a detection of a target 52 by observer 50, and for determining an existence of target 52 in the image based, at least in part, on the identification of the neurophysiological event, as further detailed hereinabove.

The method as described above can be implemented in computer software executed by system 30. For example, the software can be stored in of loaded to memory 38 and executed on CPU 36. Thus, some embodiments of the present invention comprise a computer software product which comprises a computer-readable medium, more preferably a non-transitory computer-readable medium, in which program instructions are stored. The instructions, when read by data processor 32, cause data processor 32 to execute the method as described above.

Alternatively, the computation capabilities of system 30 can be provided by dedicated circuitry. For example, CPU 30 and/or memory 46 can be integrated into dedicated circuitry configured for applying a computer vision procedure to the image to detect therein image regions suspected as being occupied by the target, thereby providing a set of candidate image regions, for presenting to an observer 50, by display 40, each candidate image region 48 as a visual stimulus, for processing the neurophysiological signals received from system 36 to identify a neurophysiological event indicative of a detection of a target 52 by observer 50, and for determining an existence of target 52 in the image based, at least in part, on the identification of the neurophysiological event, as further detailed hereinabove.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Prototype System

Despite considerable advances in computer vision, the capabilities of the human visual-perceptual system still surpasses even the best artificial intelligence systems, especially as far as its flexibility, learning capacity, and robustness to variable viewing conditions. Yet when it comes to sorting through large volumes of images, such as X-ray images of baggage screening or medical images, images of suspects from surveillance cameras, or satellite aerials, humans are generally accurate, but too slow. The bottleneck does not stem mainly from perceptual processes, which are pretty quick, but from the time it takes to register the decision, be it orally, in writing, or by a button press. To overcome this impediment, observers can be freed from the need to overtly report their decision, while a computerized algorithm sorts the pattern of their single trial brain responses, as images are presented at a very high rate.

This example describes a prototype system that implements the above task. All kinds of visual data including stills images and videos can be fed into the system. First, the images are processed by computer vision based analysis to detect potential regions of interest and to divide the images into small tiles whose size is optimized for human visual perception. Then the tiles of interest are presented at high adjustable rate to the human observer. The observer's brain responses are recorded using EEG and transferred to the processing unit where the brain responses are classified in real time. By combining classification scores from computer vision analysis and from human brain responses, the system detects images containing targets and presents them in real time to the end user.

Figure 1A:
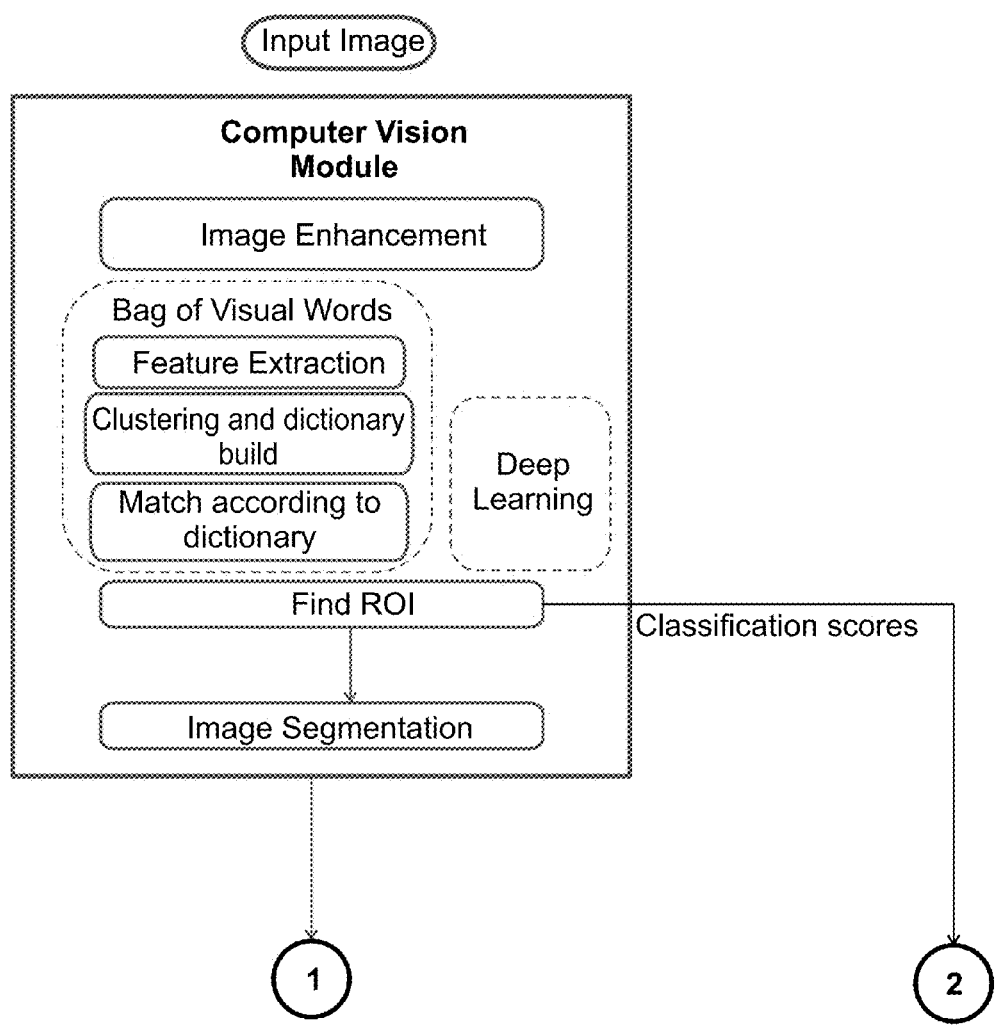
Figure 1B:
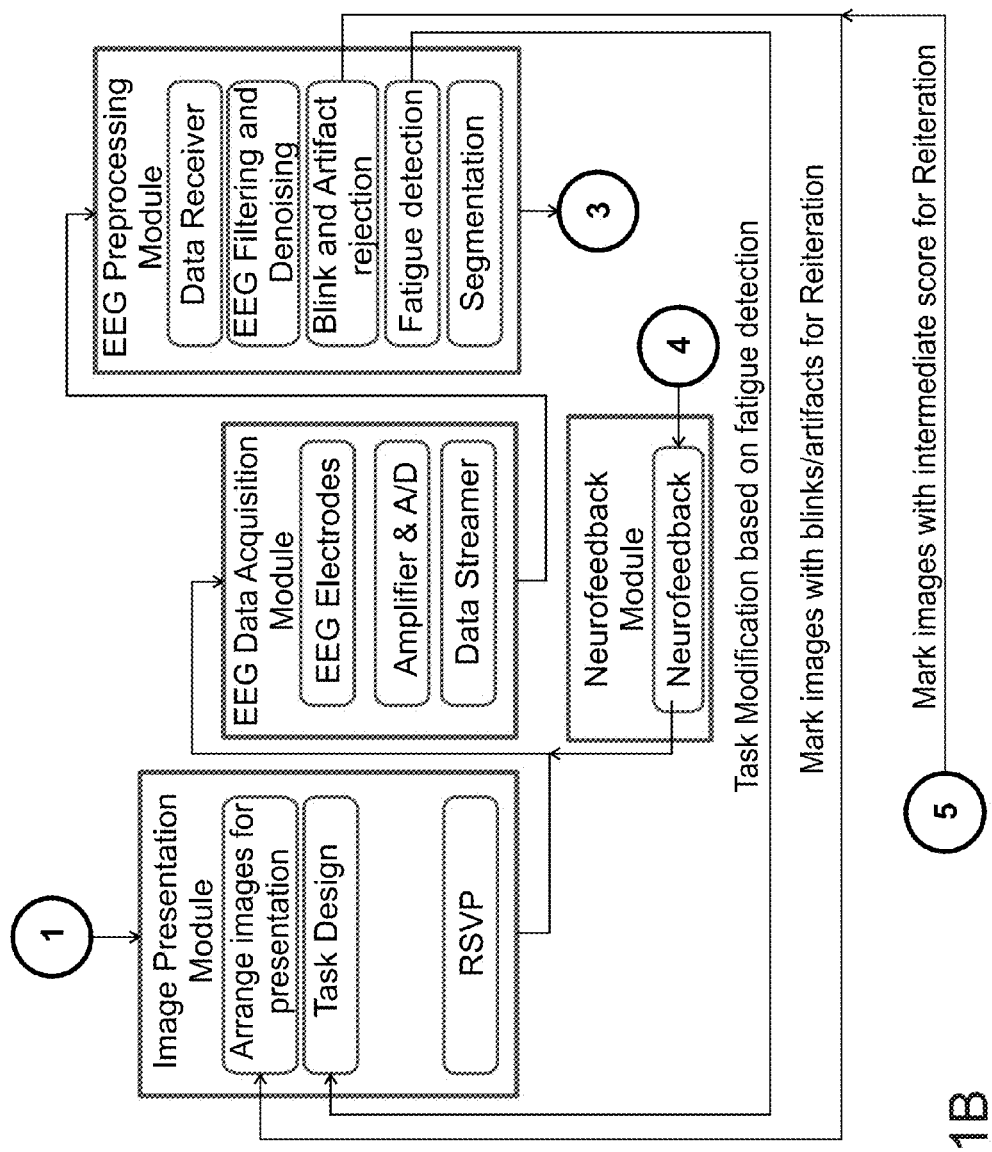
Figure 1C:
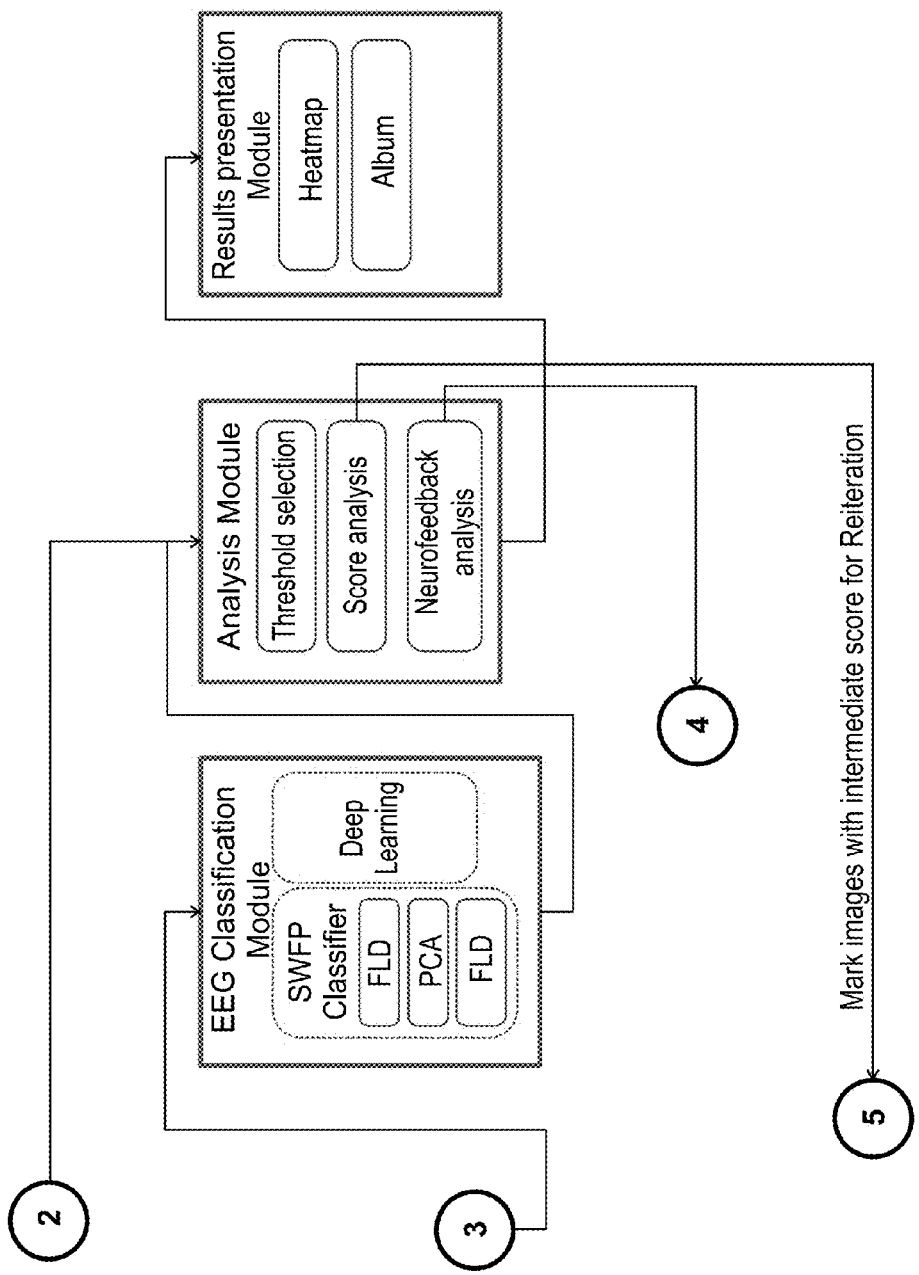

FIGS. 1A-C are block diagrams describing an image classification system, according to some embodiments of the present invention. At least one of the modules in FIGS. 1A-C is optional.

Computer Vision Module

The Computer vision module is optionally and preferably used to initially screen the input images and identify regions potentially containing targets or objects of interest, and/or regions that definitely do not contain targets or objects of interest. Images or parts of images with target probability below a pre-selected adjustable threshold will not be presented to the human observer to reduce the total inspection time. Images with target probability above the threshold are optionally and preferably divided into small tiles which size is adapted (e.g., optimized) for human visual perception. The division is optionally and preferably done in a way that includes the detected regions of interest, so as to assist the human observer to detect and inspect it faster.

The computer vision module is based on a computer vision classifier that is realized using one of the algorithms described below or their combination.

The score obtained by computer vision classifier may be combined with the score obtained by the brain responses classifier (see below) to yield higher total classification result.

Bag Of Visual Words

The algorithm can be based on Ref [1]. The image is optionally and preferably represented as "bag" of visual words, for example, patches that are described by a certain descriptor.

Figure 2A:
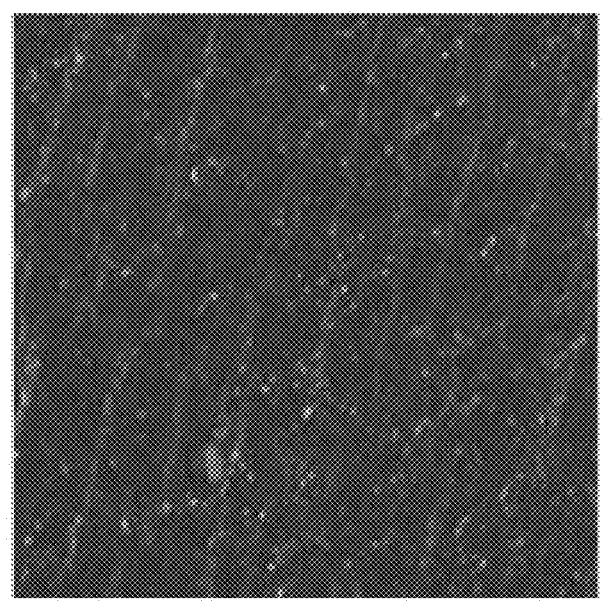
Figure 2B:
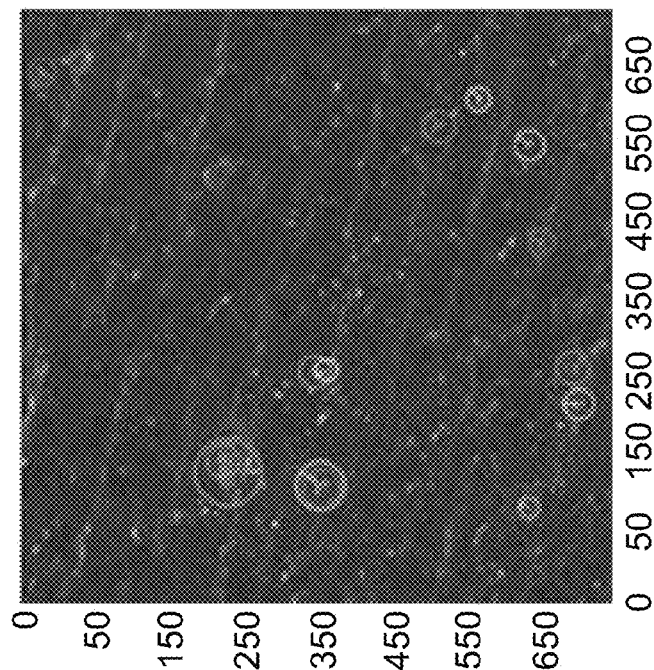

Keypoints in the image can be detected using Speeded up Robust Features (SURF) detector and described as feature vector. FIGS. 2A and 2B are examples of the descriptors extracted from aerial image of river with objects.

The image can then be described by the final number of features (clusters) to construct the "dictionary" of visual words. This is optionally and preferably performed using the unsupervised learning method of cluster analysis, such as, but not limited to, k-Means, fuzzy K-means or the like.

Each keypoint in the image can be matched to the closest visual word in the constructed dictionary. Count of visual words in the image constitutes the feature vector that is used in the training stage. Words are weighted based on their appearance frequency in the image.

A number of classifiers can be trained using the feature vector above. Classifiers can be selected from the group consisting of SVM, Adaboost, Naive Bayes. To improve the classification result, classifiers scores may optionally and preferably be combined to yield multiexpert decision.

Figure 3A:
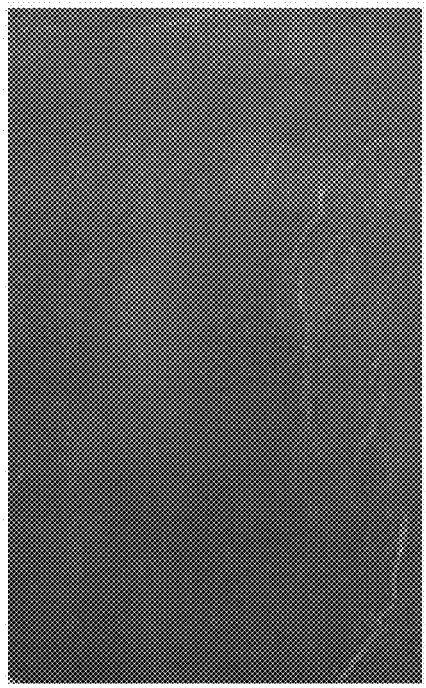
Figure 3B:
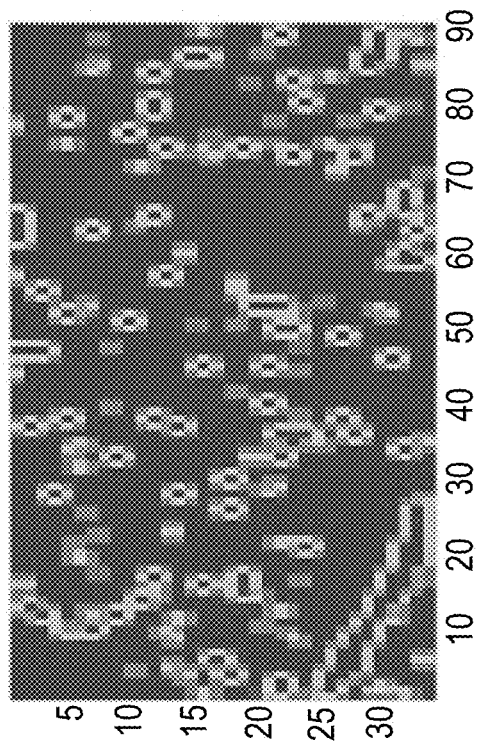

FIGS. 3A and 3B indicate the detected regions of interest in aerial image of river with objects using this algorithm.

Feature Extraction with a Sparse Autoencoder and Convolution

To train the feature extraction module, the images are used for unsupervised feature learning by an autoencoder. Small n-by-n patches are extracted, optionally and preferably randomly, from the images and each patch is concatenated to form a column vector, $\vec{v}_i$ with $n^2$ elements. Each vector is optionally and preferably passed through a two-layer neural network. The output of the first layer is $\vec{u}_i = g(W^{(1)} \cdot \vec{v}_i + \vec{b}_1)$, where $$g(x) = \frac{1}{1+e^{-x}}.$$

The matrix $W^{(1)}$ and the vector $\vec{b}_1$ have dimensions m-by-n and m-by-1, respectively. Optionally and preferably m<n. The vector $\vec{u}_i$ can be passed through the second layer so that the output is $\vec{x}_i = g(W^{(2)} \cdot \vec{u}_i + \vec{b}_2)$, where the dimensions of $W^{(2)}$ and $\vec{b}_2$, are n-by-m and n-by-1, respectively. The network can be trained, for example, by finding a parameter set $(W^{(1)}, \vec{b}_1, W^{(2)}, \vec{b}_2)$ that minimizes a cost function.

A cost function suitable to any one of the embodiments of the present invention is $$J(W^{(1)}, \vec{b}_1, W^{(2)}, \vec{b}_2) = J_{MSE} + \lambda J_{reg} + \beta J_{sparse}.$$

The first term of the cost function corresponds to the mean-square-error, $J_{MSE} = \Sigma_{j=1}^{N_p} \|\vec{x}_i - \vec{v}_i\|_2$ where $N_p$ is the number of patches. The second term is the regularization cost, $J_{reg} = \Sigma_{ij}(W_{ij}^{(1)})^2 + \Sigma_{ij}(W_{ij}^{(2)})^2$. The third term is a sparsity cost, $$J_{sparse} = \sum_{j=1}^{m} \rho \log\left(\frac{\rho}{\hat{\rho}_j}\right) + (1-\rho)\log\left(\frac{1-\rho}{1-\hat{\rho}_j}\right),$$

where $\rho$ is a fixed pre-defined parameter and $$\hat{\rho}_j = \frac{1}{N_p} \sum_{j=1}^{N_p} u_i(j),$$

where $u_i(j)$ is the j-th element of $\vec{u}_i$.

After the network has been trained, the $W^{(1)}$, $\vec{b}_1$ and can be used for feature extraction. The rows of $W^{(1)}$ are optionally and preferably reshaped to form a set of m n-by-n filters, $\{w^{(1)}\}_{i=1}^{w1}$. An image P can then be filtered by convolution with these filters to obtain a set of m filtered images, $Q^{(i)} = g(w^{(1)} \times P + b(i))$. The dimensions of each filtered image are then optionally and preferably reduced by pooling. The set of pooled images can be concatenated to form as single feature vector, $\vec{x}$. The set of feature vectors from the training images, optionally and preferably together with their labels, can be used to train a classifier.

Image Presentation Module

The images for presentation to human observer are arranged based on at least one of the following:

(a) Images preselected by the Computer Vision Module.

(b) Images whose classification score is intermediate and does not enable for deterministic decision whether they include target or not are optionally and preferably presented again to the observer and a new score is combined with the previously available score.

(c) Images returned for re-presentation by the Preprocessing Module (for example, images that were presented while eye blink or EEG artifact occurred).

(d) Images that are pre-classified that are displayed to the observer in order to allow measurement of accuracy levels, fatigue and alertness throughout the session (see below).

The images are optionally and preferably presented to the user in RSVP (Rapid Serial Visual Presentation) at a high rate that is determined based on one or more of the following: application needs, urgency, user fatigue. The rate may vary (but not limited to) from 1 Hz to 20 Hz. During the RSVP presentation the attention level, or mental fatigue of the user is optionally and preferably monitored using the following method:

Mental fatigue is optionally and preferably defined as a state of cortical deactivation, which reduces mental performance and decreases alertness. The major symptom of mental fatigue is a general sensation of weariness, feelings of inhibition, and impaired activity due to low levels of attention and concentration. The system optionally and preferably measures fatigue using a unique combination of electrophysiological markers and performance assessment on pre-classified trials. Real time spectral analyses of the EEG signal to monitor the ratio of slow wave to fast wave EEG activities over time. A representative example of such a ratio is (theta+alpha)/beta. An increase in this ratio indicates an increase in fatigue levels. In addition, muscle tone and the amount and waveform of blinks can also indicate fatigue, and these can be measured using the electrodes on the EEG cap. Pre-classified trials, in which the identity of the images is known, are entered into the RSVP stream so that the accuracy of the EEG classification can be assessed automatically during real time task performance. A combination of these measures can be used, such that more pre-classified trials can be entered into the stream when the ratio [e.g., (theta+alpha)/beta] crosses some threshold.

Once fatigue is detected, longer breaks can be automatically initiated by the task, along with a verbal or visual reminder to get up and move around, go to the bathroom or rest. A report of the fatigue measures is optionally and preferably generated to provide information regarding the optimal amount of time an analyst should spend doing the task, or which times of the day are optimal for each analyst.

The performance measures can also be used to gamify the task. Every few minutes, the analyst can be asked a (pre-defined) quantitative question regarding the task (e.g., how many targets he counted). In blocks of images where pre-classified images were inserted, the answer is known and points are awarded for accurate answers. These points can be accumulated over sessions as a personal score for personal rewards or as a competitive score against other analysts performing similar tasks.

Data Acquisition Module

Neurophysiological data, such as, but not limited to, EEG data, is collected from a multitude of channels, optionally and preferably simultaneously, and optionally and preferably at a high temporal resolution. The EEG data can be obtained using commercially available EEG acquisition systems. One of such systems can be Active 2 system (BioSemi, the Netherlands) using 64 sintered Ag/AgCl electrodes. Additional electrodes can be placed at one or more, optionally and preferably all, of the follows locations: two on the mastoid processes, two horizontal EOG channels positioned at the outer canthi of the left and right eyes (HEOGL and HEOGR, respectively), two vertical EOG channels, one below (infraorbital, VEOGI) and one above (supraorbital, VEOGS) the right eye, and a channel on the tip of the nose. Additional system can be Electrical Geodesics Inc. GES400 system with 64 electrodes set.

The data can be sampled at a sampling rate of, for example, 256 Hz with a low-pass filter of, for example, 51 Hz to prevent aliasing of high frequencies. Preferably online filtering is employed. Other sampling rates and cutoff frequencies for filtering are also contemplated. The data can be streamed to the preprocessing module using, for example, TCP link.

Preprocessing Module

The advantage of preprocessing is that it allows flexible real-time feedback or interaction, by identifying task related brain responses in single trials, and categorizing them into the associated brain states.

EEG data is received from the Acquisition module, optionally and preferably in real time, in blocks of adjustable size. The preprocessing module includes the following stages which are optionally and preferably performed sequentially on the entire block to allow real time operation:

(a) Filtering. The data is band pass filtered, for example, in the range of 0.1-30 Hz, but other frequency bands are also contemplated, to remove slow drifts and high frequency interferences.

(b) Denoising. To raise the probability of classification success, the brain responses data is optionally and preferably additionally denoised using wavelet analysis or other method.

(c) Eyeblink detection and removal (d) Artifacts rejection (e) Data segmentation. The data is segmented to one-second event-related segments starting, for example, 100 ms prior to and ending, for example, 900 ms after the onset of each image presentation. Other timings for the segmentation are also contemplated.

(f) Baseline correction. The mean activity is averaged, for example, over 100 ms prior to stimulus onset for each trial and channel independently. Other time period for averaging are also contemplated.

The preprocessed single trial brain responses are optionally and preferably arranged in spatiotemporal data matrices for the representation of single trial brain activity ready for the subsequent classification.

Training Procedure

The system is optionally and preferably trained individually for each user and learns the brain responses in order to enable real-time brain wave classification. The training can be performed by presenting pre-classified images to the user, using EEG electrodes to recording the brain responses to these images and using the recorded brain activity to train the EEG classifier. The image training set optionally and preferably contain both target and non-target images.

When classifying new images, a classifier that was trained on a different day can be used. Once the classification of the new images is verified, they can be used to improve the classifier by adding them to the training set.

Classification Module

The classification module receives spatiotemporal EEG data and classifies the brain responses based on one or more of the following methods SWFP (Spatially Weighted FLD-PCA) classifier, Deep convolutional net classifier and Multiple classifiers.

SWFP Classifier

1) Stage I:

a) Classify time points independently to compute a spatiotemporal matrix of discriminating weights (U). To implement this, take each column vector $x_{n,t}$ of the input matrix $X_n$; Each column represents the spatial distribution of EEG signals at time t, and at this step of analysis all time points are treated independently. Train a separate FLD classifier for each time point $t=1 \ldots T$, based on all $n=1 \ldots N$ trials in the training set, to obtain a spatial weight vector $w_t$ for each time point t. Set these weights vectors as the columns of the spatiotemporal weighting matrix U. The dimensions of U are the same as the dimensions of X.

b) Use this weighting matrix U to amplify the original spatiotemporal data matrix ($X_n$) by the discriminating weights at each spatiotemporal point, creating the spatially-weighted matrix $X_{wn}$. To implement this amplification, compute the Hadamard product of the trial input matrix $X_n$ and the weighting matrix U, by element-wise multiplication of the two matrices.

$$X_{wn} = U \times X_n (X_{wn})t,d = (U)t,d \cdot (X_n)t,d, t=1 \ldots T, d=1 \ldots D. \quad (1)$$

c) For dimensionality reduction of $X_{wn}$, use PCA on the temporal domain, for each spatial channel d independently, to represent the time series data as a linear combination of only K components. PCA is applied independently on each row vector $x_d$, $d=1 \ldots D$ of the spatially weighted matrix $X_{wn}$, following mean subtraction. For each roved, this provides a projection matrix $A_d$ of size T×K, which is used to project the time series data of channel d on the first K principal components; thus reducing dimensions from T to K per channel. K=6 was empirically chosen to explain >70% variance in Experiment 1. The resulting matrix $\hat{X}_n$ is of size D×K, where each row d holds the PCA coefficients for the K principal temporal projections.

$$\hat{x}_d{}^n = x_d A_d. \quad (2)$$

2) Stage II:

a) Concatenate the rows of the matrix $\hat{X}n$ to create a feature representation vector zn, representing the temporally approximated, spatially weighted activity of the single trial n.

$$zn = [\hat{x}1n \ldots \hat{x}Dn]. \quad (3)$$

b) Train and run an FLD classifier on the feature vectors $\{zn\}Nn=1$ to classify the single-trialmatrices Xn into one of two classes (using zero as the decision boundary).

$$yn = f(zn). \quad (4)$$

The most discriminative response latency is optionally and preferably defined as the latency t for which the highest percent correct classification was achieved in step 1.a. The associated discriminative spatial activation pattern is given by U(t).

Deep Convolutional Neural Network Classifier (Deep Learning)

In these embodiments the classifier is designed as a deep convolutional neural network. It receives the EEG signal as a matrix with dimensions $N_{chan} \times N_t$ ($N_{chan}$ and $N_t$ are the numbers of EEG channels and time points, respectively) and produces a score, $0 \leq p \leq 1$, which is an estimate of the probability that the presented stimulus was a target. The network can be trained using stochastic gradient descent (SGD) to minimize the logistic regression cost function.

Figure 4:
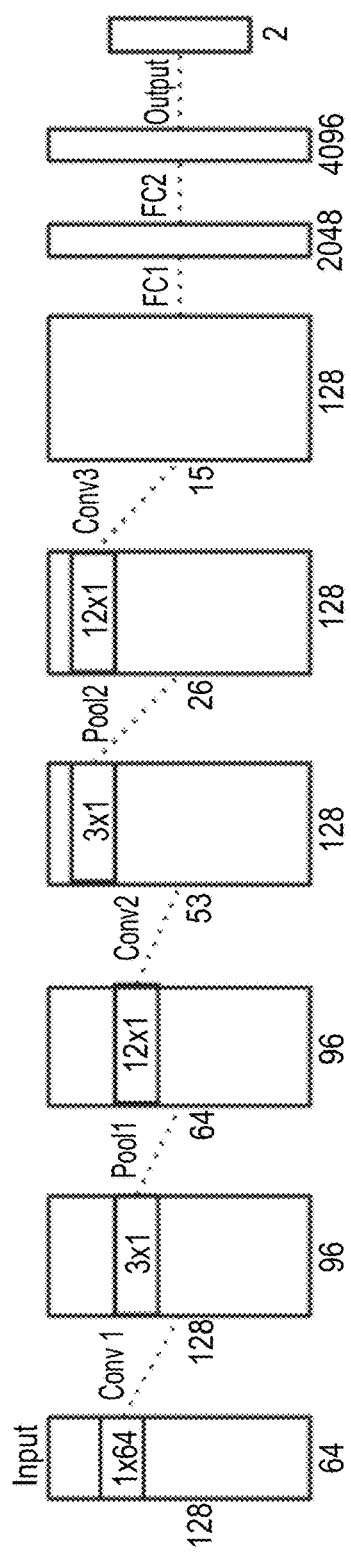

The network structure is optionally and preferably as follows (see FIG. 4):

1. A dropout layer, preferably with a 0.2 dropout ratio.
2. A convolution layer (Conv1), preferably with 96 convolution kernels of size $N_{chan} \times 1$ (these kernels perform spatial filtering for every time point).
3. A ReLU-nonlinearity layer (the input is passed through a function $f(x) = \max(x, 0)$.)
4. A max-pooling layer (Pool1), preferably with pooling kernel size 1×3 and a stride of 2.
5. A second convolution layer (Conv2), preferably with 128 kernels of size 1×6 (temporal filtering).
6. A second ReLU-nonlinearity layer.
7. A second max-pooling layer (Pool2), preferably with pooling kernel size 1×3 and a stride of 2.
8. A third convolution layer (Conv3), preferably with 128 kernels of size 1×6.
9. A third ReLU-nonlinearity layer.
10. A fully-connected layer (FC1), preferably with 2048 outputs (the input to this layer is reshaped into a column vector $\vec{v}$ and the output is $\vec{v}$ where the matrix w has 2048 rows).
11. A fourth ReLU-nonlinearity layer
12. A second dropout layer, preferably with a 0.5 dropout ratio.
13. A second fully-connected layer (FC2), preferably with 4096 outputs.
14. A fifth ReLU-nonlinearity layer
15. A third dropout layer, preferably with a 0.5 dropout ratio
16. A logistic regression layer, that computes p according to a logistic regression function, such as, but not limited to:

$$p = \frac{e^{-\vec{\theta}_1^T \vec{x}}}{e^{-\vec{\theta}_1^T \vec{x}} + e^{-\vec{\theta}_0^T \vec{x}}}$$

where $\vec{x}$ is the input vector to this layer and $\vec{\theta}_1$ and $\vec{\theta}_0$ are the layer parameter vectors.

The SCID training process is optionally and preferably performed with a learning rate of 0.001 and 0.9 momentum. Other rates and momenta are also contemplated. The training set can be modified to include the same number of "target" and "non-target" samples by bootstrapping the class with smaller number of samples to match the size of the larger class.

Multiple Classifiers

To benefit from both the SWFP and the deep convolutional net classifiers, the overall score of an image can optionally and preferably be a combination of the scores it receives from both classifiers. The SWFP algorithm employs FLD for classification, therefore the scale of the scores that this algorithm produces depends on the specific training data whereas the deep net classifier uses logistic regression and hence always produces scores in the region [0,1]. To make the scores comparable, the SWFP score, henceforth denoted as $x_{FLD}$, is optionally and preferably rescaled. For example, Gaussian functions from the training data can be use to fit the conditional probabilities $Pr(x_{FLD}|y=n)$, where y is the image label and n=0,1 for non target and target images, respectively:

$$p_n(x_{FLD}) \triangleq Pr(x_{FLD} | y = n; \mu_n, \sigma_n) = \frac{1}{\sqrt{2\pi} \, \sigma_n} e^{-\frac{(x_{FLD} - \mu_n)^2}{2\sigma_n^2}}$$

The normalized FLD score, $\tilde{x}_{FLD}$, can then be defined as $Pr(y=1|x_{FLD})$. From Bayes' formula one has:

$$Pr(y = 1 | x_{FLD}) = \frac{Pr(x_{FLD} | y = 1) \cdot Pr(y = 1)}{Pr(x_{FLD} | y = 0) \cdot Pr(y = 0) + Pr(x_{FLD} | y = 1) \cdot Pr(y = 1)}$$

In some embodiments of the present invention the prior probabilities $Pr(y=n)$ are substituted as $$Pr(y = n) = \frac{1}{2}.$$

A fitted Gaussian functions can be used to yield the normalized FLD score:

$$\tilde{x}_{FLD} = \frac{p_1(x_{FLD})}{p_0(x_{FLD}) + p_1(x_{FLD})}$$

Alternatively, the prior probabilities can be estimated.

Figure 5:
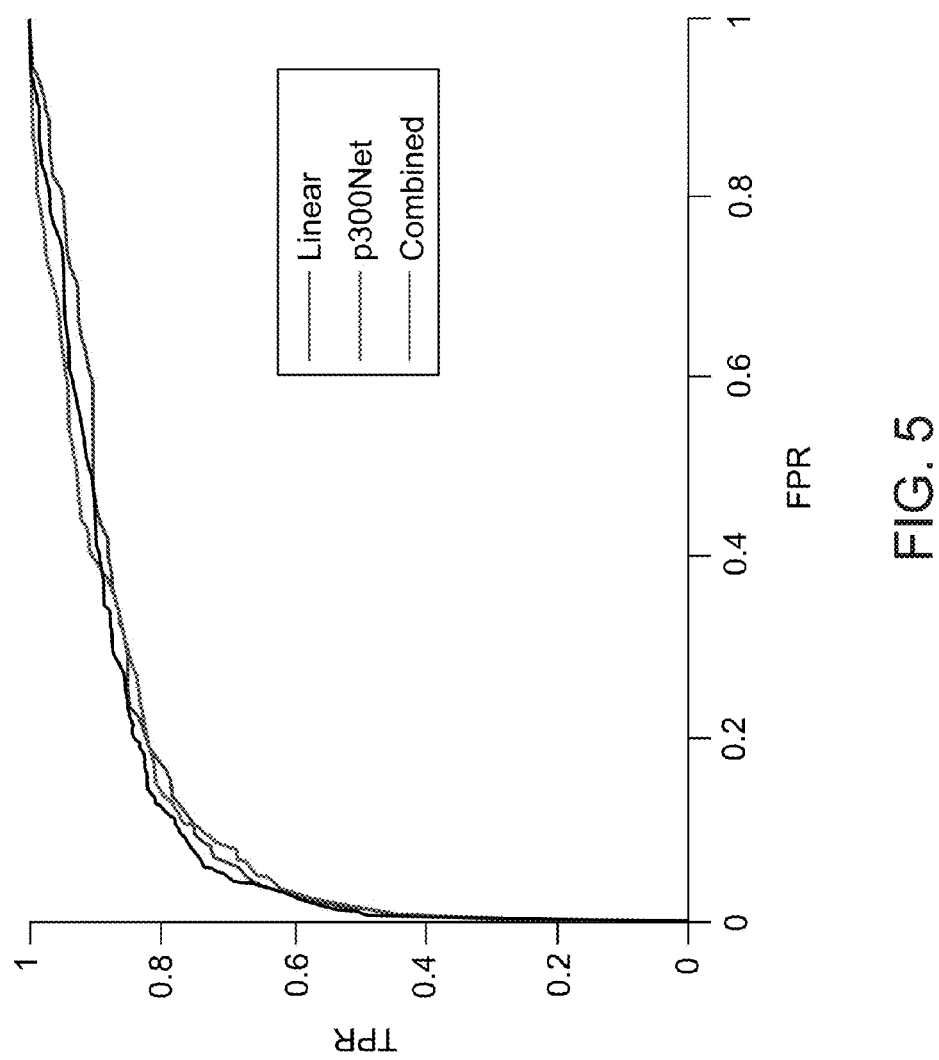

The overall score of the image can be the average of $\tilde{x}_{FLD}$ and the deep net classifier score. The ROC (FIG. 5) demonstrates the advantage of using combination of two classifiers.

Analysis Module

Figure 6:
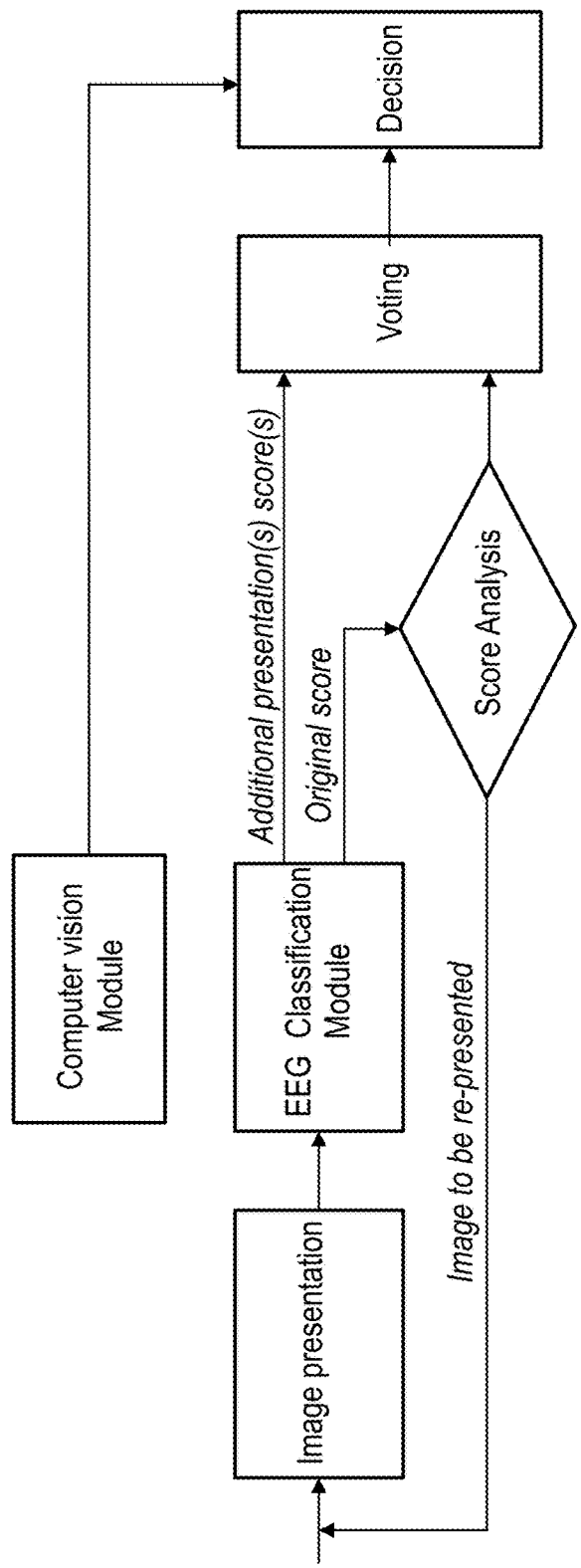

The Analysis module executes a method of analysis. A block diagram of the method executed by the Analysis module according to some embodiments of the present invention is illustrated in FIG. 6. The Analysis module receives image classification scores from the EEG classification module and from the computer vision module and performs one or more of the following activities.

Determine, based on the pre-selected score threshold, whether additional presentation of the image is required to improve the level of certainty before making the decision. The system optionally and preferably allows images that are ambiguously classified to be re-inserted into the queue of images to be shown to the user for another look. To quantify the ambiguousness of two or more classification Gaussian functions, $g_0(x;\mu_0,\sigma_0)$ and $g_1(x;\mu_1,\sigma_1)$, are used to fit the distributions of scores given by the classifier to the "target" and "non-target" training example, respectively. When a new image arrives, its score, s, is optionally and preferably normalized to a $\tilde{s}\in[0,1]$ by $$\tilde{s} = \frac{g_1(s)}{g_1(s)+g_0(s)}.$$

When $$\left|\tilde{s}-\frac{1}{2}\right|$$

is smaller than an ambiguity threshold, $T_{amb}$, the image is optionally and preferably returned to the queue for additional presentation. The threshold $T_{amb}$ can be adjusted by the user according to the requirements of the task.

After the score from the additional image presentation has been obtained, the decision is done, optionally and preferably based on voting on the EEG classification scores from all image presentations and Computer vision classification score of these images.

Neurofeedback Module

In various exemplary embodiments of the invention the Neurofeedback module is incorporated in the training procedure. Following the initial training of the classifier, the subsequent classification results are fed back to the user following every stimulus, as positive feedback for correct classification (Hits) and negative feedback for incorrect classification (False Alarms) [binary feedback], or as feedback of the classifier score [non binary feedback]. The user consequently learns how to change his/her brain responses to the stimuli as to improve the classifier's performance by aiming to increase the amount of positive feedback and reduce the amount of negative feedback. The learning process can be implicit, such that the user cannot describe explicitly what he/she is doing to improve the feedback he is receiving or explicit by having the user apply a cognitive or emotional strategy which will improve the feedback. Once the user succeeds in improving the classifier's results, the process is reiterated: new classification parameters are learnt, and again feedback is given to the user and so forth. This closed-loop process is intended to improve the accuracy of the classifier by iteratively refining the classifier's accuracy and the compatibility of the user's brain responses with the classifier's learnt assumptions. Moreover, by adapting his/her brain responses to improve the system's classification, the user's image interpretation skills are also improved, as he/she implicitly learns what the system considers a target and not a target.

Results Presentation Module

The system of the present embodiments can present the results in more than one way. Two examples are described below.

Example 1: Album

Figure 7:
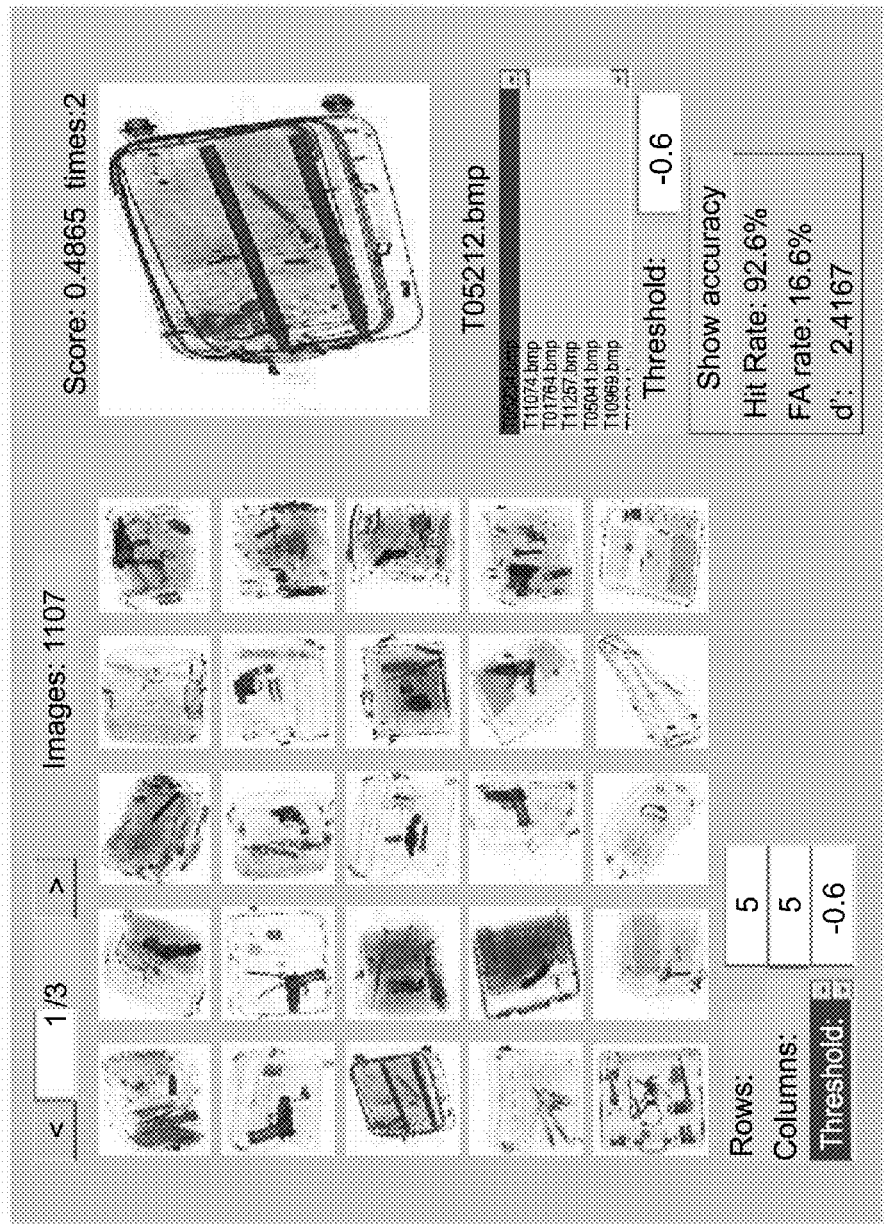

To classify a stack of individual images (e.g. X-ray images of baggage or medical images) the system of the present embodiments can arrange the images in an album (see representative screen shot in FIG. 7). Every image is given a score by the EEG classifier. The images are of the present embodiments sorted by their scores. In some embodiments of the present invention only images whose scores exceed a certain threshold T are presented on the screen and classified as targets. The threshold T can be adjusted by the user in real time.

Example 2: Spatial "Heat Map"

Figure 8:
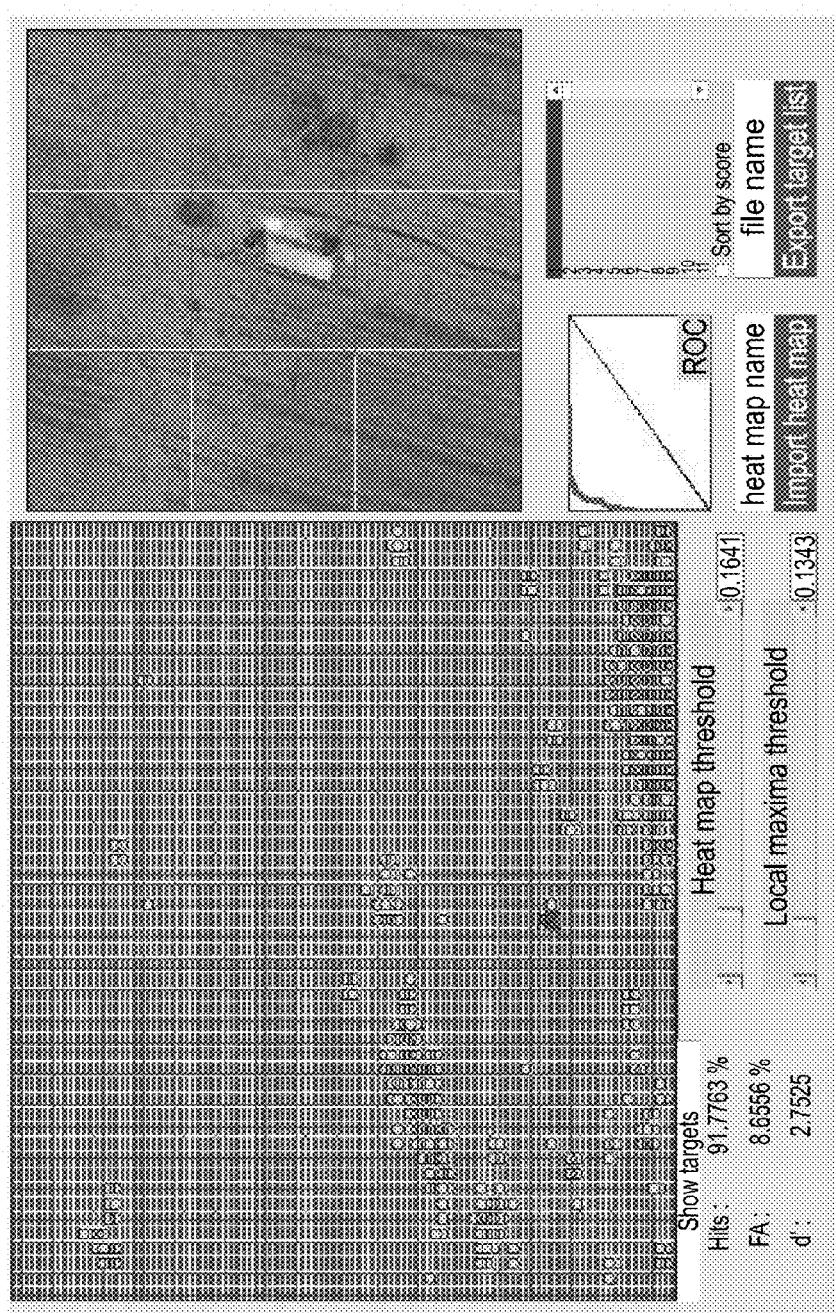

For large images such as maps, satellite footage or aerial footage, it is beneficial to use the system of the present embodiments for generating a heat map (see representative screen shot in FIG. 8). In these embodiments the image is dissected to tiles with an overlap between adjacent tiles both in the x and y directions. The overlap is optionally and preferably such that a fraction p of the tile is shared with the adjacent tile, where the fraction p is larger than some fraction threshold (e.g., p>0.5 but other values for the fraction threshold are also contemplated). Each tile can be divided to $n=(1-p)^{-2}$ parts so that each part also appears in n−1 other different tiles. For example, for a 50% overlap one has p=0.5, and each tile can be divided into quarters that also appear in 3 other tiles. The heat map is then embodied as a matrix Q such that every matrix-element $q_{ij}$ corresponds to an n-th of a tile.

To generate the spatial heat map, a score is calculated for every n-th of a tile, where the score is the average score of all tiles that contain this n-th. Thereafter a threshold T is selected as $q_{ij}$ is set as:

$$q_{ij} = \max\left(\frac{s_{ij}-T}{\max_{i,j} s_{ij}-T}, 0\right)$$

Once the heat map Q is computed, points with values higher than a second threshold, $T_{glob}$ are optionally and preferably marked as potential targets. Additional potential targets can be located by searching for local maxima of the heat map with values higher than a threshold $T_{loc}<T_{glob}$. For every location marked as a potential target, the tiles that contain it are optionally and preferably identified and marked as targets. The thresholds $T_{glob}$ and $T_{loc}$ can be modified on line by the user.

Example 2

X-Ray/CT Images

X-Ray/CT images of baggage or cargo, and medical X-Ray/CT images can be inspected using the system of the present embodiments. The prototype system described in Example 1 was successfully used to classify X-Ray images of airport checkpoint baggage to detect images containing threats (firearms and sharp objects). Following are the results of the experiment.

Brain Responses: ERP—Event Related Potentials and Spatial Distributions

Figures 9A, 9B:
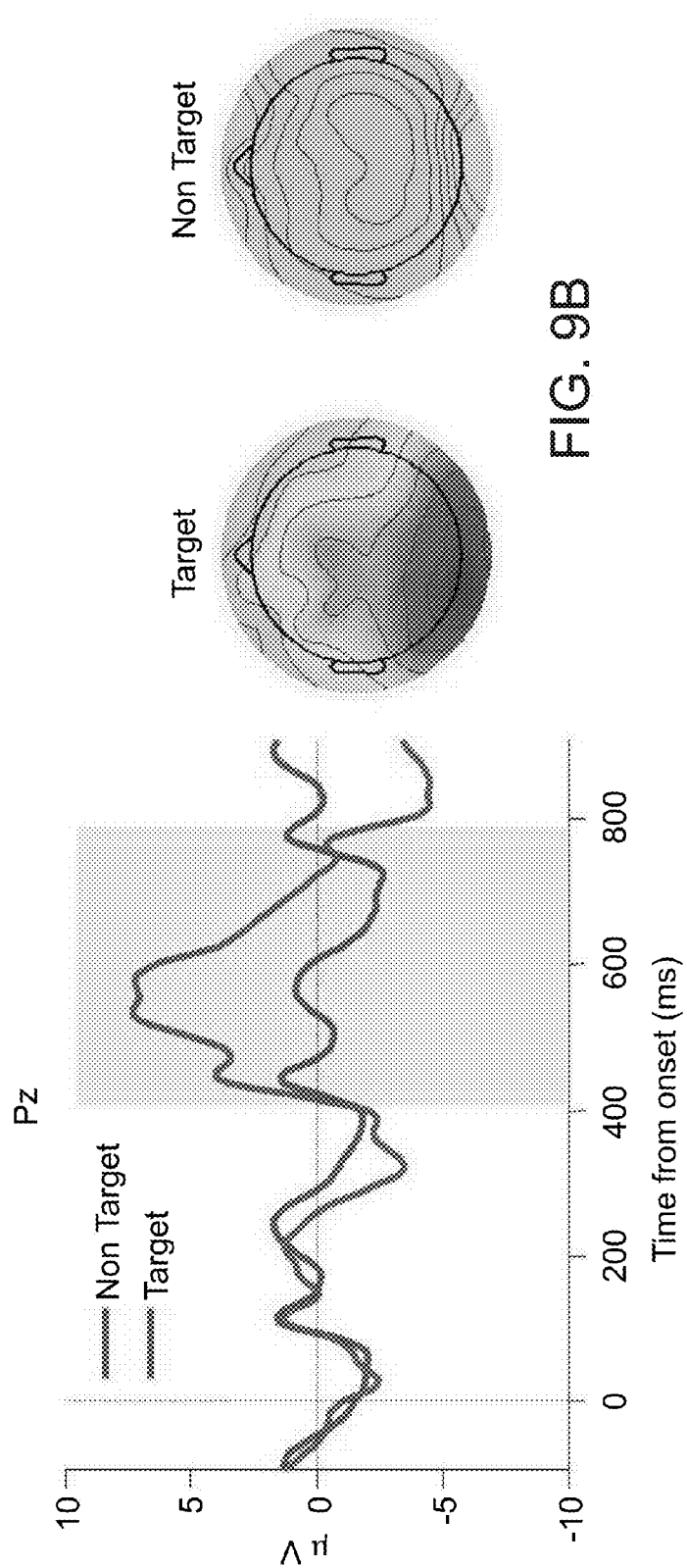

FIG. 9A shows the average brain response (ERP) to targets and non-targets at one of the EEG electrodes (Pz). FIG. 9B presents the distribution of electrical potentials on the head 400-800 milliseconds after image presentation. Reddish colors indicate high energy which is useful for classification.

Figures 10A, 10B:
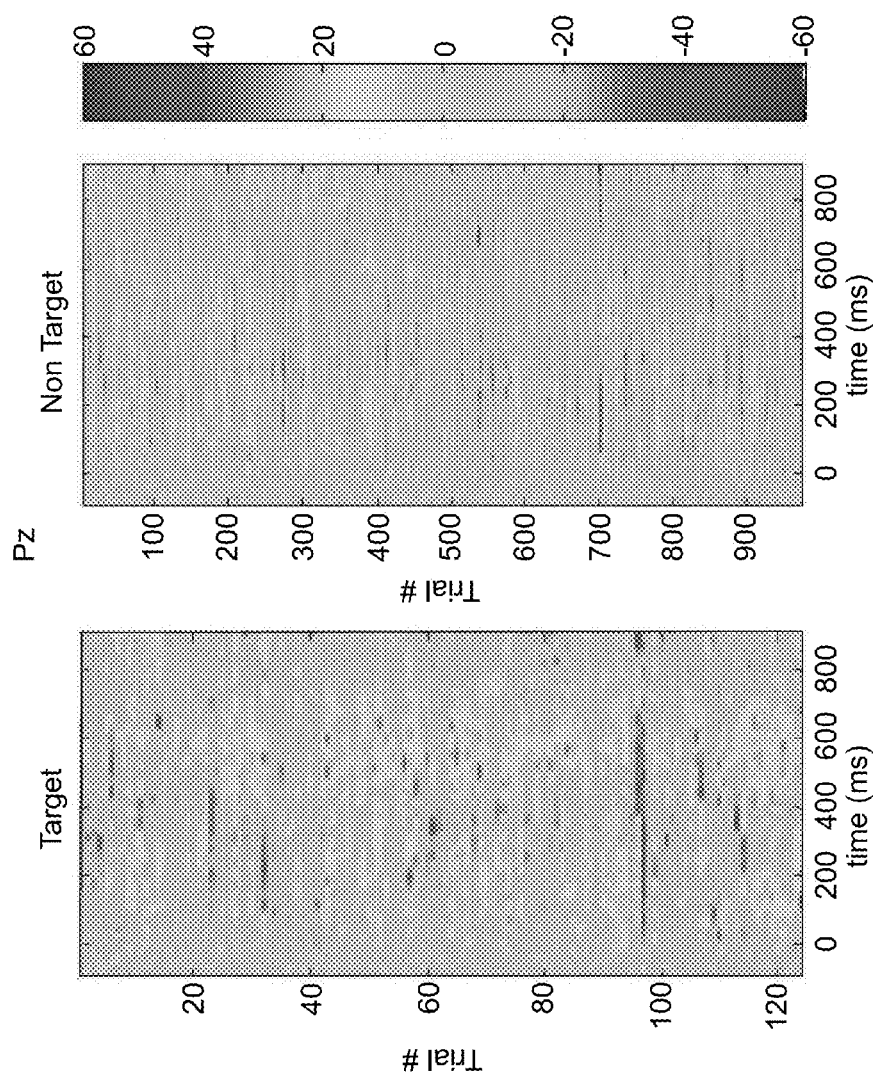

FIGS. 10A and 10B demonstrate the difference between brain responses to single images of Targets and Non-Targets measured at electrode Pz:

Scores Distribution

Every image was assigned with a classification score. FIG. 11 demonstrates scores distribution of the test phase dataset. The bags containing threats yielded overall higher classification scores than the innocent bags.

System Performance

By selecting the threshold on the classification score the images that are classified as threats and the images that are innocents are determined. Based on a given operating scenario, the threshold can be set to allow optimal trade-off between hits and false alarms, or be set to ensure, for example, 0% Misses or 0% False Alarms.

The Receiver Operating Characteristic (ROC) curve shown in FIG. 12 illustrates the performance of the classifier at different thresholds.

A different version of the same data (FIG. 13) shows how increasing or decreasing the threshold affects the hit and false alarm rates.

The system of the present embodiments can also be a useful tool to determine what baggage should be chosen for selective opening to achieve specific accuracy. For example, based on the above results, if the threshold were set to ensure 100% threat detection, the system flags about 37% of the bags for opening. To detect close to 90% of the threats, about 20% of the bags are flagged for opening. Or, with a setting requiring no false alarms at all (at the cost of detecting only ⅔ of the targets), the system flags about 7.5% of bags (all of which includes targets). The table below summarizes some of the operating points.

| Scenario | Threshold | Hits | FAs | % of Bags flagged |
|---|---|---|---|---|
| ~90% hit rate | −0.3936 | 88.9% | 10.9% | 20% |
| 0% Misses | −0.72 | 100% | 28.9% | 37% |
| 0% FAs | 0.11 | 66.7% | 0% | 7.5% |
| 25% Bags opening | −0.5 | 92.6% | 16.6% | 25% |

Example 3

Aerial Images

The system of the present embodiments can be used to interpret aerial images and detect targets or objects of interest. The prototype system described in Example 1 was successfully tested to detect buildings in aerial image of 100 square kilometers. The table below summarizes the percentage of hits/false alarms/d' in this task, where the images were presented at rates of 5 Hz (2 sessions) and 10 Hz (4 sessions) for one subject.

| subject | session | Hz | Day | Repetitions of each stimuli | Number of Targets | Number of Non Targets | Hits | FAs | d' |
|---|---|---|---|---|---|---|---|---|---|
| 101 | 1 | 5 | 1 | 2 | 606 | 9284 | 88.4% | 18.5% | 2.09 |
| | 2 | 5 | 1 | 2 | 663 | 8195 | 87.0% | 25.9% | 1.78 |
| | 3 | 10 | 1 | 2 | 664 | 8225 | 84.9% | 35.0% | 1.42 |
| | 4 | 10 | 1 | 2 | 606 | 9253 | 84.7% | 21.4% | 1.81 |
| | 5 | 10 | 2 | 4 | 1212 | 18557 | 87.5% | 9.6% | 2.45 |
| | 6 | 10 | 2 | 4 | 1330 | 16428 | 83.2% | 17.7% | 1.89 |
| 102 | 1 | 5 | 1 | 2 | 603 | 9246 | 87.9% | 14.9% | 2.21 |
| | 2 | 5 | 1 | 2 | 652 | 8134 | 86.4% | 23.3% | 1.82 |
| | 3 | 10 | 1 | 2 | 605 | 9212 | 85.3% | 20.5% | 1.87 |
| | 4 | 10 | 1 | 2 | 644 | 8005 | 83.5% | 32.2% | 1.44 |
| | 5 | 10 | 2 | 4 | 1315 | 16140 | 80.9% | 14.6% | 1.93 |
| | 6 | 10 | 2 | 4 | 1141 | 17374 | 81.8% | 6.5% | 2.42 |

FIGS. 14A and 14B demonstrate the difference between brain responses to single images of Targets and Non-Targets measured at electrode Pz.

FIGS. 15 and 16 show the average brain response (ERP) to targets and non-targets at one of the electrodes (Pz) and the distribution of electrical potentials on the head 400-800 milliseconds after image presentation. Reddish colors indicate high energy which is useful for classification.

Example 3

Face Detection

The prototype system described in Example 1 was successfully tested to detect images of certain person face among other faces images.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

[1] Csurka, Gabriella, et al, "Visual categorization with bags of keypoints." Workshop on statistical learning in computer vision, ECCV. Vol. 1. No. 1-22, 2004

[2] Single Trial detection in encephalography. U.S. Pat. No. 8,731,650

[3] Rapid image annotation via brain state decoding and visual pattern mining. U.S. Pat. No. 8,671,069

[4] System for optimal rapid serial visual presentation (RSVP) from user-specific neural brain signals. U.S. Pat. No. 8,699,767

[5] Cognitive-neural method for image analysis U.S. Pat. No. 8,214,309

[6] System for intelligent goal-directed search in large volume imagery and video using a cognitive-neural subsystem U.S. Pat. No. 8,335,751

[7] Neurophysiologically driven high speed image triage system and method. U.S. Pat. No. 7,835,581

[8] Hierarchichal rapid serial visual presentation for robust target identification. U.S. Pat. No. 8,059,136

[9] Intelligent image segmentation system and method for accurate target detection. U.S. Pat. No. 8,254,634

[10] Dynamic calibration of physiologically driven image triage systems. U.S. Pat. No. 8,271,074

[11] Target specific image scaling for effective rapid serial visual presentation. U.S. Pat. No. 7,991,195

[12] Rapid serial visual presentation triage prioritization based on user state assessment. U.S. Pat. No. 8,374,687

[13] Method and system for user sensitive pacing during rapid serial visual presentation. U.S. Patent No. 2,007, 0173699

[14] Coupling human neural response with computer pattern analysis for single-event detection of significant brain responses for task-relevant stimuli. U.S. Pat. No. 8,244,475.

The invention claimed is:

1. A method of classifying an image, comprising:
   applying a computer vision procedure to the image to detect a target therein, and assigning a computer detection score to the image using said computer vision procedure;
   presenting the image to an observer as a visual stimulus, while collecting neurophysiological signals from a brain of said observer;
   processing said neurophysiological signals to identify a neurophysiological event indicative of a detection of the target by said observer, and assigning to the image a neurophysiological detection score, based on said identification;
   determining an existence of said target in the image based on both said computer detection score and said neurophysiological detection score;
   determining a mismatch between said computer detection score and said neurophysiological detection score; and
   when said mismatch is detected, re-presenting said image to said observer.

2. The method according to claim 1, wherein said neurophysiological signals comprise EEG signals, and wherein the method comprises calculating a ratio of slow wave EEG to fast wave EEG and determining a neurophysiological state of said observer based on said ratio.

3. The method according to claim 1, wherein said computer vision procedure employs clustering.

4. The method according to claim 1, wherein said computer vision procedure employs neural networks.

5. The method according to claim 1, wherein said collecting said neurophysiological signals is at a sampling rate of at least 150 Hz.

6. The method according to claim 1, further comprising applying a low pass filter to said collected neurophysiological signals.

7. The method according to claim 1, wherein said processing said neurophysiological signals comprises applying a Spatially Weighted Fisher Linear Discriminant (SWFLD) classifier to said neurophysiological signals.

8. The method according to claim 1, wherein said processing said neurophysiological signals comprises applying a convolutional neural network (CNN) classifier to said neurophysiological signals.

9. The method according to claim 8, wherein said CNN comprises a first convolution layer applying spatial filtering for each of a plurality of time points characterizing said neurophysiological signals, a second convolution layer applying temporal filtering to outputs provided by said first convolution layer, and a third convolution layer applying temporal filtering to outputs provided by said second convolution layer.

10. The method according to claim 1, wherein said processing said neurophysiological signals comprises:
    applying a Spatially Weighted Fisher Linear Discriminant (SWFLD) classifier;
    calculating a SWFLD classification score based on said SWFLD classifier;
    applying a convolutional neural network (CNN) classifier to said neurophysiological signals;
    calculating a CNN classification score based on said CNN classifier; and
    combining said SWFLD score and said CNN score.

11. The method according to claim 1, further comprising presenting to said observer a feedback regarding said identification of said neurophysiological event.

12. The method according to claim 11, wherein said feedback is binary.

13. The method according to claim 11, wherein said feedback is non-binary.

14. The method according to claim 1, being used in a virtual reality system or an augmented reality system.

15. The method according to claim 14, further comprising varying a field-of-view provided by said virtual reality or augmented reality system, in response to said determination of said existence.

16. The method according to claim 1, being used in an augmented reality system.

17. The method according to claim 1, further comprising processing said neurophysiological signals to identify eye blinks, and re-presenting said image to said observer in response to a positive identification of said eye blink during previous presentation of said image.

18. The method according to claim 1, further comprising repeating said presentation and said identification of said neurophysiological event, comparing said identification to a previous identification of said image, and determining a neurophysiological state of said observer based on said comparison.

19. The method according to claim 1, further comprising presenting to said observer a database image containing said target, processing said neurophysiological signals to identify a neurophysiological event indicative of a detection of the target in said database image by said observer, and determining a neurophysiological state of said observer based on said identification.

20. The method according to claim 1, further comprising processing said neurophysiological signals to identify muscle tonus, and re-presenting said image to said observer in response to a positive identification of said muscle tonus during previous presentation of said image.

21. The method according to claim 1, further comprising processing said neurophysiological signals to identify eye blinks, evaluating a temporal pattern of said eye blinks and determining a neurophysiological state of said observer based on said temporal pattern.

* * * * *